United States Patent [19]
Poulsen

[11] Patent Number: 6,147,279
[45] Date of Patent: Nov. 14, 2000

[54] INHIBITION OF GENE EXPRESSION

[75] Inventor: Peter Poulsen, Copenhagen, Denmark

[73] Assignee: Danisco A/S, Copenhagen, Denmark

[21] Appl. No.: 08/981,803

[22] PCT Filed: Jul. 12, 1996

[86] PCT No.: PCT/EP96/03052

§ 371 Date: Apr. 17, 1997

§ 102(e) Date: Apr. 17, 1997

[87] PCT Pub. No.: WO97/04112

PCT Pub. Date: Feb. 6, 1997

[30] Foreign Application Priority Data

Jul. 14, 1995 [GB] United Kingdom ................. 9514435

[51] Int. Cl.$^7$ ........................ C12N 15/29; C12N 15/82; A01H 5/00; C12P 19/04
[52] U.S. Cl. ........................ 800/284; 800/286; 800/287; 800/317.2; 435/101; 435/320.1; 435/468; 536/23.6; 536/24.1; 536/24.5
[58] Field of Search .................... 800/278, 284, 800/286, 287, 298, 317.2; 435/419, 468, 320.1, 101; 536/23.6, 24.1, 24.5

[56] References Cited

U.S. PATENT DOCUMENTS

| 4,740,463 | 4/1988 | Weinberg et al. | 435/172.3 |
| 5,916,808 | 6/1999 | Kole et al. | 435/375 |

FOREIGN PATENT DOCUMENTS

| 0240208 A2 | 10/1987 | European Pat. Off. |
| WO 90/08828 | 8/1990 | WIPO. |
| WO 92/11375 | 7/1992 | WIPO. |
| WO 92/14827 | 9/1992 | WIPO. |
| WO 92/15680 | 9/1992 | WIPO. |
| WO 94/09144 | 4/1994 | WIPO. |
| WO 94/11520 | 5/1994 | WIPO. |
| WO 95/26407 | 10/1995 | WIPO. |

OTHER PUBLICATIONS

Simpson et al. "Efficient splicing of an AU–rich antisense intron sequence," Plant Mol Biol 1993 21(2):205–11 (Jan. 1993), Abstract Only.

McCullough et al. "AU–rich intronic elements affect pre–mRNA 5' splice site selection in Drosophila melanogaster," Mol Cell Biol 13(12):7689–97 (Dec. 1993), Abstract Only.

Rodriguez et al. "effects of anti–sense oligonucleotides directed toward dihydrofolate reductase RNA in mammalian cultured cells," Int J Cancer 81(5):785–92 (May 31, 1999), Abstract Only.

Sierakowska et al., "Sensitivity of splice sites to antisense oligonucleotides in vivo," RNA 5(3):369–77 (Mar. 1999), Abstract Only.

Kole, R. "Modification of pre–mRNA splicing by antisense oligonucleotides," Acta Biochim Pol 44(2):231–7 (1997), Abstract Only.

Theor. Appl. Genet., vol. 86, pp. 665–72, 1993, Shimada et al.

Plant Polymeric Carbohydrates, pp. 33–39, Jan. 7, 1993, Willmitzer et al.

Biological Abstracts vol. 121, p. 283, 1994, Abstract #101242c, Shimada et al.

Journal of Biological Chemistry, vol. 268, No. 25, pp. 19084–91, 1993, Mizuno et al.

Plant Molecular Biology, vol. 26, pp. 1759–73, 1994, Kuipers et al.

Mol. Gen. Genet., vol. 246, pp. 745–55, 1995, Kuipers et al.

Gottesman et al. 1990, Proc. Natl. Acad. Sci. USA 87:3513–3517.

Pritchard et al. 1983, J. Mol. Biol. 164:1–15.

Merkelbach et al. 1993, Plant Mol. Biol. 23(4): 881–888.

Kawasaki et al. 1993, Mol. Gen. Genet., 237:10–16.

Poulsen et al. 1993, Plant Physiol. 102(3):1053–1054.

*Primary Examiner*—David T. Fox
*Attorney, Agent, or Firm*—Frommer Lawrence & Haug LLP; Thomas J. Kowalski

[57] ABSTRACT

A method of inhibiting gene expression is described. The method, which affects enzymatic activity in a plant. The method includes expressing in a plant, or a cell, a tissue or an organ thereof, a nucleotide sequence wherein the nucleotide sequence codes, partially or completely, for an intron in an antisense orientation; and wherein the nucleotide sequence does not contain a sequence that is antisense to an axon sequence normally associated with the intron.

23 Claims, 19 Drawing Sheets

Reducing end

Reducing end

```
         10        20        30        40        50        60
1234567890123456789012345678901234567890123456789012345678901234567890
ATCATGGCCAATTACTGGTTCAAATGCATTACTTCCTTTCAGATTCTTTCGAGTTCTCAT    60
GACCGGTCCTACTACAGACGATACTAACCCGTGGAACTGTTGCATCTGCTTCTTAGAACT   120
CTATGGCTATTTTCGTTAGCTTGGCGTCGGTTTGAACATAGTTTTTGTTTTCAAACTCTT   180
CATTTACAGTCAAAATGTTGTATGGTTTTTGTTTTCCTCAATGATGTTTACAGTGTTGTG   240
TTGTCATCTGTACTTTTGCCTATTACTTGTTTTGAGTTACATGTTAAAAAAGTGTTTATT   300
TTGCCATATTTTGTTCTCTTATTATTATTATCATACATACATTATTACAAGGAAAAGACA   360
AGTACACAGATCTTAACGTTTATGTTCAATCAACTTTTGGAGGCATTGACAGGTACCACA   420
AATTTTGAGTTTATGATTAAGTTCAATCTTAGAATATGAATTTAACATCTATTATAGATG   480
CATAAAAATAGCTAATGATAGAACATTGACATTTGGCAGAGCTTAGGGTATGGTATATCC   540
AACGTTAATTTAGTAATTTTTGTTACGTACGTATATGAAATATTGAATTAATCACATGAA   600
CGGTGGATATTATATTATGAGTTGGCATCAGCAAAATCATTGGTGTAGTTGACTGTAGTT   660
GCAGATTTAATAATAAAATGGTAATTAACGGTCGATATTAAAATAACTCTCATTTCAAGT   720
GGGATTAGAACTAGTTATTAAAAAAATGTATACTTTAAGTGATTTGATGGCATATAATTT   780
AAAGTTTTTCATTTCATGCTAAAATTGTTAATTATTGTAATGTAGACTGCGACTGGAATT   840
ATTATAGTGTAAATTTATGCATTCAGTGTAAAATTAAAGTATTGAACTTGTCTGTTTTAG   900
AAAATACTTTATACTTTAATATAGGATTTTGTCATGCGAATTTAAATTAATCGATATTGA   960
ACACGGAATACCAAAATTAAAAAGGATACACATGGCCTTCATATGAACCGTGAACCTTTG  1020
ATAACGTGGAAGTTCAAAGAAGGTAAAGTTTAAGAATAAACTGACAAATTAATTTCTTTT  1080
ATTTGGCCCACTACTAAATTTGCTTTACTTTCTAACATGTCAAGTTGTGCCCTCTTAGTT  1140
GAATGATATTCATTTTTCATCCCATAAGTTCAATTTGATTGTCATACCACCCATGATGTT  1200
CTGAAAAATGCTTGGCCATTCACAAAGTTTATCTTAGTTCCTATGAACTTTATAAGAAGC  1260
TTTAATTTGACATGTTATTTATATTAGATGATATAATCCATGACCCAATAGACAAGTGTA  1320
TTAATATTGTAACTTTGTAATTGAGTGTGTCTACATCTTATTCAATCATTTAAGGTCATT  1380
AAAATAAATTATTTTTTGACATTCTAAAACTTTAAGCAGAATAAATAGTTTATCAATTAT  1440
TAAAAACAAAAAACGACTTATTTATAAATCAACAAACAATTTTAGATTGCTCCAACATAT  1500
```

```
         10        20        30        40        50        60
123456789012345678901234567890123456789012345678901234567890
TTTTCCAAATTAAATGCAGAAAATGCATAATTTTATACTTGATCTTTATAGCTTATTTTT   1560
TTTAGCCTAACCAACGAATATTTGTAAACTCACAACTTGATTAAAAGGGATTTACAACAA   1620
GATATATATAAGTAGTGACAAATCTTGATTTTAAATATTTTAATTTGGAGGTCAAAATTT   1680
TACCATAATCATTTGTATTTATAATTAAATTTTAAATATCTTATTTATACATATCTAGTA   1740
AACTTTTAAATATACGTATATACAAAATATAAAATTATTGGCGTTCATATTAGGTCAATA   1800
AATCCTTAACTATATCTGCCTTACCACTAGGAGAAAGTAAAAAACTCTTTACCAAAAATA   1860
CATGTATTATGTATACAAAAAGTCGATTAGATTACCTAAATAGAAATTGTATAACGAGTA   1920
AGTAAGTAGAAATATAAAAAAACTACAATACTAAAAAAAATATGTTTTACTTCAATTTCG   1980
AAACTAATGGGGTCTGAGTGAAATATTCAGAAAGGGGAGGACTAACAAAAGGGTCATAAT   2040
GTTTTTTTATAAAAAGCCACTAAAATGAGGAAATCAAGAATCAGAACATACAAGAAGGCA   2100
GCAGCTGAAGCAAAGTACCATAATTTAATCAATGGAAATTAATTTCAAAGTTTTATCAAA   2160
                                     M  E  I  N  F  K  V  L  S  K
ACCCATTCGAGGATCTTTTCCATCTTTCTCACCTAAAGTTTCTTCAGGGgtaattttac   2220
 P  I  R  G  S  F  P  S  F  S  P  K  V  S  S  G
taatttcatgttaatttcaattattttagcctttgcatttcattttccaatatatctgg   2280
atcatctccttagttttttattttatttttataatatcaaatatggaagaaaaatgaca   2340
cttgtagagccatatgtaagtatcatgtgacaaatttgcaaggtggttgagtgtataaaa   2400
ttcaaaaattgagagatggagggggggtgggggbaragacaatatttagaaagagtgttc   2460
taggaggttatggaggacacggatgaggggtagaaggttagttaggtatttgagtgttgt   2520
ctggcttatcctttcatactagtagtcgtggaattatttgggtagtttcttgttttgtta   2580
tttgatctttgttattctatttctgtttcttgtacttcgattattgtattatatatctt   2640
gtcgtagttattgttcctcggtaagaatgctctagcatgcttcctttagtgttttatcat   2700
gccttctttatattcgcgttgctttgaaatgcttttactttagccgagggtctattagaa   2760
acaatctctctatctcgtaaggtaggggtaaagtcctcaccacactccacttgtgggatt   2820
acattgtgtttgttgttgtaaatcaattatgtatacataatangtggattttttacaaca   2880
caaatacatggtcaagggcaaagttctgaacacataaagggttcattatatgtccaggga   2940
tatgataaaaattgtttctttgtgaaagttatataagatttgttatggcttttgctggaa   3000
```

```
          10        20        30        40        50        60
 1234567890123456789012345678901234567890123456789012345678901234567890
 acataataagttataatgctgagatagctactgaagtttgttttttctagccttttaaat          3060 gtaccaataatagattccgtatcgaacgagtatgttttgattacctggtcatgatgtttc          3120 tattttttacattttttggtgttgaactgcaattgaaaatgttgtatcctatgagacgg          3180 atagttgagaatgtgttctttgtatggaccttgagaagctcaaacgctactccaataatt         3240 tctatgaattcaaattcagttatggctaccagtcagtccagaaattaggatatgctgca          3300 tatacttgttcaattatactgtaaaatttcttaagttctcaagatatccatgtaacctcg         3360 agaatttcttttgacagGCTTCTAGAAATAAGATATGTTTTCCTTCTCAACATAGTACTGG         3420
                   A S R N K I C F P S Q H S T G
 ACTGAAGTTTGGATCTCAGGAACGGTCTTGGGATATTTCTTCCACCCCAAAATCAAGAGT          3480
 L K F G S Q E R S W D I S S T P K S R V
 TAGAAAAGATGAAAGGgtatgtttgataatttatatggttgcatggatagtatataaata         3540
 R K D E R
 gttggaaaacttctggactggtgctcatggcatatttgatctgtgcaccgtgtggagatg         3600 tcaaacatgtgttacttcgttccgccaatttataatacttaacttgggaaagacagctc          3660 tttactcctgtgggcatttgttatttgaattacaatctttatgagcatggtgttttcaca         3720 ttatcaacttctttcatgtggtatataacagttttagctccgttaataccttttcttctt         3780 tttgatataaactaactgtggtgcattgcttgcbkkkATGAAGCACAGTTCAGCTATTTC         3840
                                      M K H S S A I S
 CGCTGTTTTGACCGATGACGACAATTCGACAATGGCACCCCTAGAGGAAGATGTCAAGAC          3900
 A V L T D D D N S T M A P L E E D V K T
 TGAAAATATTGGCCTCCTAAATTTGGATCCAACTTTGGAACCTTATCTAGATCACTTCAG         3960
 E N I G L L N L D P T L E P Y L D H F R
 ACACAGAATGAAGAGATATGTGGATCAGAAAATGCTCATTGAAAAATATGAGGGACCCCT         4020
 H R M K R Y V D Q K M L I E K Y E G P L
 TGAGGAATTTGCTCAAGgtaacagccaaaagttgtgctttaggcagtttgaccttattt          4080
 E E F A Q G
 ggaagatgaattgtttatacctactttgactttgctagagaattttgcataccggggagt        4140 aagtagtggctccatttaggtggcacctggccattttttgatcttttaaaaagctgttt          4200 gattgggtcttcaaaaaagtagacaaggttttggagaagtgacacacccccggagtgtc         4260 agtggcaaagcaaagatttcactaaggagattcaaaatataaaaaaagtatagacataa         4320 agaagctgagggattcaacatgtactatacaagcatcaaatatagtcttaaagcaatt          4380 tgtagaaataaagaaagtcttccttctgttgcttcacaatttccttctattatcatgagt        4440 tactctttctgttcgaaatagcttccttaatattaaattcatgatacttttgttgagatt        4500
```

```
                10        20        30        40        50        60
       1234567890123456789012345678901234567890123456789012345678901234567890
       tagcagttttttcttgtgtaaactgctctcttttttgcagGTTATTTAAAATTTGGATT              4560
                                                Y  L  K  F  G  F
       CAACAGGGAAGATGGTTGCATAGTCTATCGTGAATGGGCTCCTGCTGCTCAgtaggtcct             4620
        N  R  E  D  G  C  I  V  Y  R  E  W  A  P  A  A  Q
       cgtctactacaaaatagtagtttccatcatcataacagattttcctattaaagcatgatg            4680
       ttgcagcatcattggctttcttacatgttctaattgctattaaggttatgcttctaatta            4740
       actcatccacaatgcagGGAAGCAGAAGTTATTGGCGATTTCAATGGATGGAACGGTTCT             4800
                          E  A  E  V  I  G  D  F  N  G  W  N  G  S
       AACCACATGATGGAGAAGGACCAGTTTGGTGTTTGGAGTATTAGAATTCCTGATGTTGAC             4860
        N  H  M  M  E  K  D  Q  F  G  V  W  S  I  R  I  P  D  V  D
       AGTAAGCCAGTCATTCCACACAACTCCAGAGTTAAGTTTCGTTTCAAACATGGTAATGGA             4920
        S  K  P  V  I  P  H  N  S  R  V  K  F  R  F  K  H  G  N  G
       GTGTGGGTAGATCGTATCCCTGCTTGGATAAAGTATGCCACTGCAGACGCCACAAAGTTT             4980
        V  W  V  D  R  I  P  A  W  I  K  Y  A  T  A  D  A  T  K  F
       GCAGCACCATATGATGGTGTCTACTGGGACCCACCACCTTCAGAAAGgttttgttattca            5040
        A  A  P  Y  D  G  V  Y  W  D  P  P  P  S  E  R
       taccttgaagctgaattttgaacaccatcatcacaggcatttcgattcatgttcttacta            5100
       gtcttgttatgtaagacattttgaaatgcaaaagttaaaataattgtgtctttactaatt            5160
       tggacttgatcccatactctttcccttaacaaaatgagtcaattctataagtgcttgaga            5220
       acttactacttcagcaattaaacagGTACCACTTCAAATACCCTCGCCCTCCCAAACCCC             5280
                                 Y  H  F  K  Y  P  R  P  P  K  P  R
       GAGCCCCACGAATCTATGAAGCACATGTCGGCATGAGCAGCTCTGAGCCACGTGTAAATT             5340
        A  P  R  I  Y  E  A  H  V  G  M  S  S  S  E  P  R  V  N  S
       CGTATCGTGAGTTTGCAGATGATGTTTTACCTCGGATTAAGGCAAATAACTATAATACTG             5400
        Y  R  E  F  A  D  D  V  L  P  R  I  K  A  N  N  Y  N  T  V
       TCCAGTTGATGGCCATAATGGAACATTCTTACTATGGATCATTTGGATATCATGTTACAA             5460
        Q  L  M  A  I  M  E  H  S  Y  Y  G  S  F  G  Y  H  V  T  N
       ACTTTTTTGCTGTGAGCAGTAGATATGGAAACCCGGAGGACCTAAAGTATCTGATAGATA             5520
        F  F  A  V  S  S  R  Y  G  N  P  E  D  L  K  Y  L  I  D  K
       AAGCACATAGCTTGGGTTTACAGGTTCTGGTGGATGTAGTTCACAGTCATGCAAGCAATA             5580
        A  H  S  L  G  L  Q  V  L  V  D  V  V  H  S  H  A  S  N  N
       ATGTCACTGATGGCCTCAATGGCTTTGATATTGGCCAAGGTTCTCAAGAATCCTACTTTC             5640
        V  T  D  G  L  N  G  F  D  I  G  Q  G  S  Q  E  S  Y  F  H
       ATGCTGGAGAGCGAGGGTACCATAAGTTGTGGGATAGCAGGCTGTTCAACTATGCCAATT             5700
        A  G  E  R  G  Y  H  K  L  W  D  S  R  L  F  N  Y  A  N  W
       GGGAGGTTCTTCGTTTCCTTCTTTCCAACTTGAGGTGGTGGCTAGAAGAGTATAACTTTG             5760
        E  V  L  R  F  L  L  S  N  L  R  W  W  L  E  E  Y  N  F  D
       ACGGATTTCGATTTGATGGAATAACTTCTATGCTGTATGTTCATCATGGAATCAATATGG             5820
        G  F  R  F  D  G  I  T 'S  M  L  Y  V  H  H  G  I  N  M  G
       GATTTACAGGAAACTATAATGAGTATTTCAGCGAGGCTACAGATGTTGATGCTGTGGTCT             5880
        F  T  G  N  Y  N  E  Y  F  S  E  A  T  D  V  D  A  V  V  Y
       ATTTAATGTTGGCCAATAATCTGATTCACAAGATTTTCCCAGATGCAACTGTTATTGCCG             5940
        L  M  L  A  N  N  L  I  H  K  I  F  P  D  A  T  V  I  A  E
       AAGATGTTTCTGGTATGCCGGGCCTTGGCCGGCCTGTTTCTGAGGGAGGAATTGGTTTTG             6000
        D  V  S  G  M  P  G  L  G  R  P  V  S  E  G  G  I  G  F  V
```

```
              10        20        30        40        50        60
     1234567890123456789012345678901234567890123456789012345678901234567890
     TTTACCGCCTGGCAATGGCAATCCCAGATAAGTGGATAGATTATTTAAAGAATAAGAATG           6060
      Y  R  L  A  M  A  I  P  D  K  W  I  D  Y  L  K  N  K  N  D
     ATGAAGATTGGTCCATGAAGGAAGTAACATCGAGTTTGACAAATAGGAGATATACAGAGA           6120
      E  D  W  S  M  K  E  V  T  S  S  L  T  N  R  R  Y  T  E  K
     AGTGTATAGCATATGCGGAGACCCATGATCAGgtattttaaatttatttctacaactaaa           6180
      C  I  A  Y  A  E  T  H  D  Q
     taattctcagaacaattgttagatagaatccaaatatatacgtcctgaaagtataaaagt           6240 acttattttcgccatgggccttcagaatattggtagccgctgaatatcatgataagttat           6300 ttatccagtgacatttttatgttcactcctattatgtctgctggatacagTCTATTGTTG           6360
                                                       S  I  V  G
     GTGACAAGACCATTGCATTTCTCCTAATGGACAAAGAGATGTATTCTGGCATGTCTTGCT           6420
      D  K  T  I  A  F  L  L  M  D  K  E  M  Y  S  G  M  S  C  L
     TGACAGATGCTTCTCCTGTTGTTGATCGAGGAATTGCGCTTCACAAGgtttgtctgtttc           6480
      T  D  A  S  P  V  V  D  R  G  I  A  L  H  K
     tattgcatttaaggttcatataggttagccacggaaaatctcactctttgtgaggtaac           6540 cagggttctgatggattattcaatttctcgtttatcatttgtttattcttttcatgcat           6600 tgtgtttcttttcaatatccctcttatttggaggtaattttctcatctattcactttt            6660 agcttctaaccacagATGATCCATTTTTTCACAATGGCCTTGGGAGGAGAGGGGTACCTC           6720
                     M  I  H  F  F  T  M  A  L  G  G  E  G  Y  L
     AATTTCATGGGTAACGAGgtatgtcttacatctttagatatttgtgataattacaatta           6780
      N  F  M  G  N  E
     gtttggcttacttgaacaagattcattcctcaaaatgacctgaactgttgaacatcaaag         6840 gggttgaaacatagaggaaaacaacatgatgaatgtttccattgtctagggatttctatt         6900 atgttgctgagaacaaatgtcatcttaaaaaaaacattgtttacttttttgtagtataga         6960 agattactgtatagagtttgcaagtgtgtctgttttggagtaattgtgaaatgtttgatg         7020 aacttgtacagTTTGGCCATCCTGAGTGGATTGACTTCCCTAGAGAGGGCAATAATTGGA          7080
                F  G  H  P  E  W  I  D  F  P  R  E  G  N  N  W  S
     GTTATGACAAATGTAGACGCCAGTGGAACCTCGCGGATAGCGAACACTTGAGATACAAGg         7140
      Y  D  K  C  R  R  Q  W  N  L  A  D  S  E  H  L  R  Y  K
     ttcaagtatttgaatcgcagcttgttaaataatctagtaattttagattgcttacttg            7200 gaagtctacttggttctggggatgatagctcatttcatcttgttctacttattttccaac         7260 cgaatttctgatttttgtttcgagatccaagtattagattcatttacacttattaccgcc         7320 tcatttctaccactaaggccttgatgagcagcttaagttgattctttgaagctatagttt         7380 caggctaccaatccacagcctgctatatttgttggatacttaccttttctttacaatgaa         7440 gtgatactaattgaaatggtctaaatctgatatctatatttctccgtctttcctccccct         7500
```

```
          10        20        30        40        50        60
 1234567890123456789012345678901234567890123456789012345678901234567890
catgatgaaatgcagTTTATGAATGCATTTGATAGAGCTATGAATTCGCTCGATGAAAAG    7560
               F  M  N  A  F  D  R  A  M  N  S  L  D  E  K
TTCTCATTCCTCGCATCAGGAAAACAGATAGTAAGCAGCATGGATGATGATAATAAGgta    7620
 F  S  F  L  A  S  G  K  Q  I  V  S  S  M  D  D  D  N  K
aaatcatctaaagttgaaagtgttgggtttatgaagtgcttcaattctatccaaggacaa    7680 gtagaaaccttttttaccttccatttcttgatgatggatttcatattatttaatccaatag  7740 ctggtcaaattcggtaatagctgtactgattagttacttcactttgcagGTTGTTGTGTT   7800
                                                 V  V  V  F
TGAACGTGGTGACCTGGTATTTGTATTCAACTTCCACCCAAAGAACACATACGAAGGgta    7860
 E  R  G  D  L  V  F  V  F  N  F  H  P  K  N  T  Y  E  G
tatatgttttacttatccatgaaattattgctctgcttgttttaatgtactgaacaagt    7920 tttatggagaagtaactgaaacaaatcattttcacattgtctaatttaactctttttct   7980 gatcctcgcatgacgaaaacagGTATAAAGTTGGATGTGACTTGCCAGGGAAGTACAGAG    8040
                       Y  K  V  G  C  D  L  P  G  K  Y  R  V
TTGCACTGGACAGTGATGCTTGGGAATTTGGTGGCCATGGAAGAgtaaggatttgcttga    8100
 A  L  D  S  D  A  W  E  F  G  G  H  G  R
ataacttttgataataagataacagatgtagggtacagttctctcaccaaaaagaactgt   8160 aattgtctcatccatctttagttgtataagatatccgactgtctgagttcggaagtgttt   8220 gagcctcctgccctccccctgcgttgtttagctaattcaaaaaggagaaaactgtttatt   8280 gatgatctttgtcttcatgctgacatacaatctgttctcatgacagACTGGTCATGATGT   8340
                                               T  G  H  D  V
TGACCATTTCACATCACCAGAAGGAATACCTGGAGTTCCAGAAACAAATTTCAATGGTCG    8400
 D  H  F  T  S  P  E  G  I  P  G  V  P  E  T  N  F  N  G  R
TCCAAATTCCTTCAAAGTGCTGTCTCCTGCGCGAACATGTGTGgtacagttcttgccgtg    8460
 P  N  S  F  K  V  L  S  P  A  R  T  C  V
tgacctccctttttattgtggttttgttcatagttatttgaatgcgatagaagttaacta   8520 ttgattaccgccacaatcgccagttaagtcctctgaactactaatttgaaaggtaggaat   8580 agccgtaataaggtctacttttggcatcttactgttacaaaacaaaaggatgccaaaaaa   8640 attcttctctatcctctttttccctaaaccagtgcatgtagcttgcacctgcataaactt   8700 aggtaaatgatcaaaaatgaagttgatgggaacttaaaaccgccctgaagtaaagctagg   8760 aatagtcatataatgtccacctttggtgtctgcgctaacatcaacaacaacatacctcgt   8820 gtagtcccacaaagtggtttcaggggagggtagagtgtatgcaaaacttactcctatct   8880 cagaggtagagaggatttttttcaatagacccttggctcaagaaaaaaagtccaaaaagaa  8940 gtaacagaagtgaaagcaacatgtgtagctaaagcgacccaacttgtttgggactgaagt   9000
```

```
          10        20        30        40        50        60
 1234567890123456789012345678901234567890123456789012345678901234567890
agttgttgttgttgaaacagtgcatgtagatgaacacatgtcagaaaatggacaacacag            9060 ttattttgtgcaagtcaaaaaaatgtactactatttctttgtgcagctttatgtatagaa            9120 aagttaaataactaatgaattttgctagcagaaaaatagcttggagagaaattttttata            9180 ttgaactaagctaactatattcatctttcttttgcttcttcttctccttgtttgtgaag            9240
GCTTATTACAGAGTTGATGAACGCATGTCAGAAACTGAAGATTACCAGACAGACATTTGT            9300
 A  Y  Y  R  V  D  E  R  M  S  E  T  E  D  Y  Q  T  D  I  C
AGTGAGCTACTACCAACAGCCAATATCGAGGAGAGTGACGAGAAACTTAAAGATTCGTTA            9360
 S  E  L  L  P  T  A  N  I  E  E  S  D  E  K  L  K  D  S  L
TCTACAAATATCAGTAACATTGACGAACGCATGTCAGAAACTGAAGTTTACCAGACAGAC            9420
 S  T  N  I  S  N  I  D  E  R  M  S  E  T  E  V  Y  Q  T  D
ATTTCTAGTGAGCTACTACCAACAGCCAATATTGAGGAGAGTGACGAGAAACTTAAAGAT            9480
 I  S  S  E  L  L  P  T  A  N  I  E  E  S  D  E  K  L  K  D
TCGTTATCTACAAATATCAGTAACATTGATCAGACTGTTGTAGTTTCTGTTGAGGAGAGA            9540
 S  L  S  T  N  I  S  N  I  D  Q  T  V  V  V  S  V  E  E  R
GACAAGGAACTTAAAGATTCACCGTCTGTAAGCATCATTAGTGATGTTGTTCCAGCTGAA            9600
 D  K  E  L  K  D  S  P  S  V  S  I  I  S  D  V  V  P  A  E
TGGGATGATTCAGATGCAAACGTCTGGGGTGAGGACTAGTCAGATGATTGATCGACCCTT            9660
 W  D  D  S  D  A  N  V  W  G  E  D
CTACCGATTGGTGATCGCTATCCTTGCTCTCTGAGAAATAGGTGAGGCGAAACAAAAAAT            9720

AATTTGCATGATAAAAAGTCTGATTTTATGATCGCTATCCTCGCTCTCTGAGAAAGAAGC            9780

GAAACAAAGGCGACTCCTGGACTCGAATCTATAAGATAACAAAGGCGACTCCTGGGACTC            9840

GAATCTATAAGATAACAAAGGCAATTCCAAGACTTGAATCTATAAAAAATTTAGTTAAGA            9900

ATGATTAACGTCCGATCCTAATTCGAATCGAGGCATCTTACCACTCCATTGATAATTATA            9960

TAAGTCAATAAGTCATATAAWAGTATTAAAAACTAAATTGACTTGATCGGTCTATCAAAA            10020

ATMAGATMAAATTGTGTTCATATGTAACATTTTTGTTGTCACAATTAGCTTAATTACATC            10080

TTTCATGTGCAATAACAAAGAAATGATAGGAATTTAGAGATTCCAATTTTTTTGTTGCCA            10140

CAATTAACTTAATTACATCTTTCATTTGCAATAACAAAGAAATGATAGGAATTTAGAGAT            10200

CCAGTGTCAATACACAACCTAGGCCAACATCGAAAGCATAACTGTAAACTCATGCATGAA            10260

GAAATCAGTCGTAAAAATGAATAAATGCGACATAAAAACAAATTGCATGTATCATTAATG            10320

TGACTTAACTACAAGTAAAAATAAATTTAACAAATGTAACTTAACTACAAGTAAAAATAA            10380

ATTGCTTCTATCATTAACAAACAAACAGAATTAAAAAGAAAAAAACATACTAAATCTTAC            10440

CGTCATTCGATAAAAAAAAATACCAAATTCATAATGCAAGGAAAACGAAACGCGTCCTGA            10500
```

```
          10        20        30        40        50        60
 1234567890123456789012345678901234567890123456789012345678901234567890
 TCGGGTATCAACGATGAAATGGACCAGTTGGATCGACTGCCTGCACAACGTTAGGTATGC    10560
 CAAAAAAAAGAACACGATCCTTTGCACCCGTTCGATGATTATCAGTATGTTCACAAAAAA    10620
 AACTTAAGTTCATCCCAGTGTACAACAGCCCCAACATCTGCCCCAAGTAACAAAAAACAA    10680
 CCAATTTATCTTATTCTTATCTGCCACAAAATAATCGGTTTCACACTATTCTCTTGTTAT    10740
 ACAAAATTGACAAGTAGGAAGGAGAGGAGTCATCCAAATAAACGGTGCACGTTCTTTGAG    10800
 AAAAGTCTTATTTTTCGTAAGATCCAATTTCAACAAACTTTTCTTCAAGTCAAAATTCCT    10860
 GATAGTGTATCTCCTCTCGACGACCTCTTGCATTGAACGATCTCCGCTTATCATGAAAAG    10920
 TTGCTTGGATAACAAGTATTGCAAGGGGGGACAGTAGCTATTAAGTTAGTCGGCCCAAG    10980
 GAAATGGAGGAGTGATAGTCTCGAATATTATTCACCTCTTTAGCATTACCCGGTCTGGCT    11040
 TTAAGGAGTTACGTCTTTTACGCTCGCCAATTTCTTTTTTTAGAATGGTTGGTGTCAAAA    11100
 TCGCGAGTTGTGGAAGGTTCAAGTTACTCGATTCGTGATTTTCAAGTATGAGTGGTGAGA    11160
 GAGATTCGATATTTTCACGAGGTGTATTCGAGGTCTAGTAGAACGAAGGGTGTCACTAAT    11220
 GAAAGTTTCAAGAGTTCATCATCATCTTCTTCTAGTAGATTTTCGCTTTCAAATGAGTAT    11280
 GAAAATTCTTCCTCTTTTCTATTGATTTTCTTCATTGTTTTCTTCATTGTTGTGGTTGTT    11340
 ATTGAAAAGAAAGAAAATTTATAACAGAAAAAGATGTCAAAAAAAAGGTAAAATGAAAGA    11400
 GTATCATATACTTAAAGAGTTGCGTAGAGATAAGTCAAAAGAAACAGAATTATAGTAATT    11460
 TCAGCTAAGTTAGAATTC                                              11478
```

INHIBITION OF GENE EXPRESSION

This application is a 371 of PCT/EP96/03052 filed Jul. 12, 1996.

FIELD OF THE INVENTION

The present invention relates to a method of inhibiting gene expression, particularly inhibiting gene expression in a plant. The present invention also relates to a nucleotide sequence useful in the method. In addition, the present invention relates to a promoter that is useful for expressing the nucleotide sequence.

Starch is one of the main storage carbohydrates in plants, especially higher plants. The structure of starch consists of amylose and amylopectin. Amylose consists essentially of straight chains of α-1-4-linked glycosyl residues. Amylopectin comprises chains of α-1-4-linked glycosyl residues with some α-1-6 branches. The branched nature of amylopectin is accomplished by the action of inter alia an enzyme commonly known as the starch branching enzyme ("SBE"). SBE catalyses the formation of branch points in the amylopectin molecule by adding α-1,4 glucans through α-1,6-glucosidic branching linkages. The biosynthesis of amylose and amylopectin is schematically shown in FIG. 1, whereas the α-1-4-links and the α-1-6 links are shown in FIG. 2.

It is known that starch is an important raw material. Starch is widely used in the food, paper, and chemical industries. However, a large fraction of the starches used in these industrial applications are post-harvest modified by chemical, physical or enzymatic methods in order to obtain starches with certain required functional properties.

Within the past few years it has become desirable to make genetically modified plants which could be capable of producing modified starches which could be the same as the post-harvest modified starches. It is also known that it may be possible to prepare such genetically modified plants by expression of antisense nucleotide coding sequences. In this regard, June Bourque provides a detailed summary of anti-sense strategies for the genetic manipulations in plants (Bourque 1995 Plant Science 105 pp 125–149). At this stage, reference could be made to FIG. 3 which is a schematic diagram of one of the proposed mechanisms of antisense-RNA inhibition.

In particular, WO 92/11375 reports on a method of genetically modifying potato so as to form amylose-type starch. The method involves the use of an anti-sense construct that can apparently inhibit, to a varying extent, the expression of the gene coding for formation of the branching enzyme in potato. The antisense construct of WO 92/11375 consists of a tuber specific promoter, a transcription start sequence and the first exon of the branching enzyme in antisense direction. However, WO 92/11375 does not provide any antisense sequence data. In addition, WO 92/11375 only discloses the use of the potato GBSS promoter.

WO 92/14827 reports on a plasmid that, after insertion into the genome of a plant, can apparently cause changes in the carbohydrate concentration and carbohydrate composition, such as the concentration and composition of amylose and amylopectin, in the regenerated plant. The plasmid contains part of the coding sequence of a branching enzyme in an antisense orientation.

EP-A-0647715 reports on the use of antisense endogenous mRNA coding DNA to alter the characteristics and the metabolic pathways of ornamental plants.

EP-A-0467349 reports on the expression of sequences that are antisense to sequences upstream of a promoter to control gene expression.

EP-A-0458367 and U.S. Pat. No. 5,107,065 report on the expression of a nucleotide sequence to regulate gene expression in a plant. The nucleotide sequence is complementary to a mRNA sequence of a gene and may cover all or a portion of the non-coding region of the gene. In other words, the nucleotide sequences of EP-A-0458367 and U.S. Pat. No. 5,107,065 must at least comprise a sequence that is complementary to a coding region. EP-A-0458367 and U.S. Pat. No. 5107065 contain minimal sequence information.

Kuipers et al in Mol. Gen. Genet. [1995] 246 745–755 report on the expression of a series of nucleotides that are antisense to part of the genomic intron sequences of potato granule bound starch synthetase. Here the antisense intron sequences are attached to a part of the antisense exon sequences—wherein the intron sequences and the exon sequences are naturally associated with each other. In addition, the expressed antisense intron sequences are at most 231 bp in length.

Likewise, Kull et al in J. Genet & Breed. [1995] 49 69–76 report on the expression of a series of nucleotides that are antisense to part of the genomic intron sequences of potato granule bound starch synthetase. Likewise, here the antisense intron sequences are attached to a part of the antisense exon sequences—wherein the intron sequences and the exon sequences are naturally associated with each other. In addition, likewise, the expressed antisense intron sequences are at most 231 bp in length.

Shimada et al in Theor. Appl. Genet. [1993] 86 665–672 report on the expression of a series of nucleotides that are antisense to part of the genomic intron sequences of rice granule bound starch synthetase. Here the antisense intron sequences are attached to a part of the antisense exon sequences—wherein the intron sequences and the exon sequences are naturally associated with each other. In addition, the expressed antisense intron sequences are less than 350 bp in length.

Reviews on how enzymatic activity can be affected by expression of particular nucleotide sequences may be found in the teachings of Finnegan and McElroy [1994] Biotechnology 12 883–888; and Matzke and Matzke [1995] TIG 11 1–3.

Whilst it is known that enzymatic activity can be affected by expression of particular nucleotide sequences there is still a need for a method that can more reliably and/or more efficiently and/or more specifically affect enzymatic activity.

SUMMARY OF THE INVENTION

According to a first aspect of the present invention there is provided a method of affecting enzymatic activity in a plant (or a cell, a tissue or an organ thereof) comprising expressing in the plant (or a cell, a tissue or an organ thereof) a nucleotide sequence wherein the nucleotide sequence partially or completely codes for (is) an intron in an antisense orientation; and wherein the nucleotide sequence does not contain a sequence that is antisense to an exon sequence normally associated with the intron.

According to a second aspect of the present invention there is provided a method of affecting enzymatic activity in a starch producing organism (or a cell, a tissue or an organ thereof) comprising expressing in the starch producing organism (or a cell, a tissue or an organ thereof) a nucleotide sequence wherein the nucleotide sequence codes, partially or completely, for an intron in an antisense orientation; and wherein starch branching enzyme activity is affected and/or the levels of amylopectin are affected and/or the composition of starch is changed.

According to a third aspect of the present invention there is provided an antisense sequence comprising the nucleotide sequence shown as any one of SEQ.I.D. No. 15 to SEQ.I.D. No. 27 or a variant, derivative or homologue thereof.

According to a fourth aspect of the present invention there is provided a promoter comprising the sequence shown as SEQ.I.D. No. 14 or a variant, derivative or homologue thereof.

According to a fifth aspect of the present invention there is provided a construct capable of comprising or expressing the present invention.

According to a sixth aspect of the present invention there is provided a vector comprising or expressing the present invention.

According to a seventh aspect of the present invention there is provided a cell, tissue or organ comprising or expressing the present invention.

According to an eighth aspect of the present invention there is provided a transgenic starch producing organism comprising or expressing the present invention.

According to a ninth aspect of the present invention there is provided a starch obtained from the present invention.

According to a tenth aspect of the present invention there is provided pBEA8 (NCIMB 40753) or pBEA9 (NCIMB 40815).

According to an eleventh aspect of the present invention there is provided a nucleotide sequence that is antisense to any one or more of the intron sequences obtainable from λ-SBE 3.2 (NCIMB 40751) or λ-SBE 3.4 (NCIMB 40752) or a variant, derivative or homologue thereof.

NCIMB 40753, NCIMB 40751, and NCIMB 40752 were deposited with The National Collections of Industrial and Marine Bacteria Limited (NCIMB), 23, St. Machar Drive, Aberdeen, Scotland, AB2 1RY, United Kingdom, under the terms of Budapest Treaty, on Jul. 13, 1995; and, NCIMB 40815 was deposited with the NCIMB under the terms of the Budapest Treaty, on Jul. 9, 1996.

A key advantage of the present invention is that it provides a method for preparing modified starches that is not dependent on the need for post-harvest modification of starches. Thus the method of the present invention obviates the need for the use of hazardous chemicals that are normally used in the post-harvest modification of starches.

In addition, the present invention provides inter alia genetically modified plants which are capable of producing modified and/or novel and/or improved starches whose properties would satisfy various industrial requirements.

Thus, the present invention provides a method of preparing tailor-made starches in plants which could replace the post-harvest modified starches.

Also, the present invention provides a method that enables modified starches to be prepared by a method that can have a more beneficial effect on the environment than the known post-harvest modification methods which are dependent on the use of hazardous chemicals and large quantities of energy.

An other key advantage of the present invention is that it provides a method that may more reliably and/or more efficiently and/or more specifically affect enzymatic activity when compared to the known methods of affecting enzymatic activity. With regard to this advantage of the present invention it is to be noted that there is some degree of homology between coding regions of SBEs. However, there is little or no homology with the intron sequences of SBEs.

Thus, antisense intron expression provides a mechanism to affect selectively the expression of a particular SBE. This advantageous aspect could be used, for example, to reduce or eliminate a particular SBE enzyme and replace that enzyme with another enzyme which can be another branching enzyme or even a recombinant version of the affected enzyme or even a hybrid enzyme which could for example comprise part of a SBE enzyme from one source and at least a part of another SBE enzyme from another source. This particular feature of the present invention is covered by the combination aspect of the present invention which is discussed in more detail later.

Thus the present invention provides a mechanism for selectively affecting SBE activity. This is in contrast to the prior art methods which are dependent on the use of for example antisense exon expression whereby it would not be possible to introduce new SBE activity without affecting that activity as well.

Preferably with the first aspect of the present invention starch branching enzyme activity is affected and/or wherein the levels of amylopectin are affected and/or the composition of starch is changed.

Preferably with the second aspect of the present invention the nucleotide sequence does not contain a sequence that is antisense to an exon sequence normally associated with the intron.

Preferably with the fourth aspect of the present invention the promoter is in combination with a gene of interest ("GOI").

Preferably the enzymatic activity is reduced or eliminated.

Preferably the nucleotide sequence codes for at least substantially all of at least one intron in an antisense orientation.

Preferably the nucleotide sequence codes, partially or completely, for two or more introns and wherein each intron is in an anti-sense orientation.

Preferably the nucleotide sequence comprises at least 350 nucleotides (e.g. at least 350 bp), more preferably at least 500 nucleotides (e.g. at least 500 bp).

Preferably the nucleotide sequence comprises the sequence shown as any one of SEQ. I.D. No. 15 to SEQ.I.D. No. 27 or a variant, derivative or homologue thereof, including combinations thereof.

Preferably the nucleotide sequence is expressed by a promoter having a sequence shown as SEQ. I.D. No 14 or a variant, derivative or homologue thereof.

Preferably the transgenic starch producing organism is a plant.

A preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in an antisense orientation; wherein the nucleotide sequence does not contain a sequence that is antisense to an exon sequence normally associated with the intron; and wherein starch branching enzyme activity is affected and/or the levels of amylopectin are affected and/or the composition of starch is changed.

A more preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in an antisense orientation; wherein the nucleotide sequence does not contain a sequence that is antisense to an exon sequence normally associated with the intron; wherein starch branching enzyme activity is affected and/or the levels of amylopectin are affected and/or the composition of starch is changed; and wherein the nucleotide sequence comprises the sequence shown as any one of SEQ.I.D. No. 15 to SEQ.I.D. No. 27 or a variant, derivative or homologue thereof, including combinations thereof.

The term "nucleotide" in relation to the present invention includes DNA and RNA. Preferably it means DNA, more preferably DNA prepared by use of recombinant DNA techniques.

The term "intron" is used in its normal sense as meaning a segment of nucleotides, usually DNA, that does not encode part or all of an expressed protein or enzyme.

The term "exon" is used in its normal sense as meaning a segment of nucleotides, usually DNA, encoding part or all of an expressed protein or enzyme.

Thus, the term "intron" refers to gene regions that are transcribed into RNA molecules, but which are spliced out of the RNA before the RNA is translated into a protein. In contrast, the term "exon" refers to gene regions that are transcribed into RNA and subsequently translated into proteins.

The terms "variant" or "homologue" or "fragment" in relation to the nucleotide sequence of the present invention include any substitution of, variation of, modification of, replacement of, deletion of or addition of one (or more) nucleic acid from or to the respective nucleotide sequence providing the resultant nucleotide sequence can affect enzyme activity in a plant, or cell or tissue thereof, preferably wherein the resultant nucleotide sequence has at least the same effect as any one of the antisense sequences shown as SEQ.I.D. No.s 15–27. In particular, the term "homologue" covers homology with respect to similarity of structure and/or similarity of function providing the resultant nucleotide sequence has the ability to affect enzymatic activity in accordance with the present invention. With respect to sequence homology (i.e. similarity), preferably there is more than 80% homology, more preferably at least 85% homology, more preferably at least 90% homology, even more preferably at least 95% homology, more preferably at least 98% homology. The above terms are also synonymous with allelic variations of the sequences.

Likewise, the terms "variant" or "homologue" or "fragment" in relation to the promoter of the present invention include any substitution of, variation of, modification of, replacement of, deletion of or addition of one (or more) nucleic acid from or to the respective promoter sequence providing the resultant promoter sequence allows expression of a GOI, preferably wherein the resultant promoter sequence has at least the same effect as SEQ.I.D. No. 14. In particular, the term "homologue " covers homology with respect to similarity of structure and/or similarity of function providing the resultant promoter sequence has the ability to allow for expression of a GOI, such as a nucleotide sequence according to the present invention. With respect to sequence homology (i.e. similarity), preferably there is more than 80% homology, more preferably at least 85% homology, more preferably at least 90% homology, even more preferably at least 95% homology, more preferably at least 98% homology. The above terms are also synonymous with allelic variations of the sequences.

The term "antisense" means a nucleotide sequence that is complementary to, and can therefore hybridize with, any one or all of the intron sequences of the present invention, including partial sequences thereof.

With the present invention, the antisense intron can be complementary to an entire intron of the gene to be inhibited. However, in some circumstances, partial antisense sequences may be used (i.e. sequences that are not or do not comprise the full complementary sequence) providing the partial sequences affect enzymatic activity. Suitable examples of partial sequences include sequences that are shorter than any one of the full antisense sequences shown as SEQ.I.D.No.s 15 to 27 but which comprise nucleotides that are at least antisense to the sense intron sequences adjacent the respective exon or exons.

With regard to the second aspect of the present invention (i.e. specifically affecting SBE activity), the nucleotide sequences of the present invention may comprise one or more sense or antisense exon sequences of the SBE gene, including complete or partial sequences thereof, providing the nucleotide sequences can affect SBE activity, preferably wherein the nucleotide sequences reduce or eliminate SBE activity. Preferably, the nucleotide sequence of the second aspect of the present invention does not comprise an antisense exon sequence.

The term "vector" includes an expression vector and a transformation vector. The term "expression vector" means a construct capable of in vivo or in vitro expression. The term "transformation vector" means a construct capable of being transferred from one species to another—such as from an *E. Coli* plasmid to a fungus or a plant cell, or from an Agrobacterium to a plant cell.

The term "construct"—which is synonymous with terms such as "conjugate", "cassette" and "hybrid"—in relation to the antisense nucleotide sequence aspect of the present invention includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. The terms do not cover the natural combination of the wild type SBE gene when associated with the wild type SBE gene promoter in their natural environment.

The construct may even contain or express a marker which allows for the selection of the genetic construct in, for example, a plant cell into which it has been transferred. Various markers exist which may be used in, for example, plants—such as mannose. Other examples of markers include those that provide for antibiotic resistance—e.g. resistance to G418, hygromycin, bleomycin, kanamycin and gentamycin.

The construct of the present invention preferably comprises a promoter. The term "promoter" is used in the normal sense of the art, e.g. an RNA polymerase binding site in the Jacob-Monod theory of gene expression. Examples of suitable promoters are those that can direct efficient expression of the nucleotide sequence of the present invention and/or in a specific type of cell. Some examples of tissue specific promoters are disclosed in WO 92/11375.

The promoter could additionally include conserved regions such as a Pribnow Box or a TATA box. The promoters may even contain other sequences to affect (such as to maintain, enhance, decrease) the levels of expression of the nucleotide sequence of the present invention. Suitable examples of such sequences include the Sh1-intron or an ADH intron. Other sequences include inducible elements—such as temperature, chemical, light or stress inducible elements. Also, suitable elements to enhance transcription or translation may be present. An example of the latter element is the TMV 5' leader sequence (see Sleat Gene 217 [1987] 217–225; and Dawson Plant Mol. Biol. 23 [1993] 97).

As mentioned, the construct and/or the vector of the present invention may include a transcriptional initiation region which may provide for regulated or constitutive expression. Any suitable promoter may be used for the transcriptional initiation region, such as a tissue specific promoter. In one aspect, preferably the promoter is the patatin promoter or the E35S promoter. In another aspect, preferably the promoter is the SBE promoter.

If, for example, the organism is a plant then the promoter can be one that affects expression of the nucleotide sequence in any one or more of seed, tuber, stem, sprout, root and leaf tissues, preferably tuber. By way of example, the promoter for the nucleotide sequence of the present invention can be the α-Amy 1 promoter (otherwise known as the Amy 1 promoter, the Amy 637 promoter or the α-Amy 637 promoter) as described in our co-pending UK patent application No. 9421292.5 filed Oct. 21, 1994. Alternatively, the promoter for the nucleotide sequence of the present invention can be the α-Amy 3 promoter (otherwise known as the Amy 3 promoter, the Amy 351 promoter or the α-Amy 351 promoter) as described in our co-pending UK patent application No. 9421286.7 filed Oct. 21, 1994.

The present invention also encompasses the use of a promoter to express a nucleotide sequence according to the present invention, wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the nucleotide sequence of the present invention in a more specific manner such as in just one specific tissue type or organ. The term "inactivated" means partial inactivation in the sense that the expression pattern of the promoter is modified but wherein the partially inactivated promoter still functions as a promoter. However, as mentioned above, the modified promoter is capable of expressing a gene coding for the enzyme of the present invention in at least one (but not all) specific tissue of the original promoter. Examples of, partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

The construct and/or the vector of the present invention may include a transcriptional termination region.

The nucleotide according to the present invention can be expressed in combination (but not necessarily at the same time) with an additional construct. Thus the present invention also provides a combination of constructs comprising a first construct comprising the nucleotide sequence according to the present invention operatively linked to a first promoter; and a second construct comprising a GOI operatively linked to a second promoter (which need not be the same as the first promoter). With this aspect of the present invention the combination of constructs may be present in the same vector, plasmid, cells, tissue, organ or organism. This aspect of the present invention also covers methods of expressing the same, preferably in specific cells or tissues, such as expression in just a specific cell or tissue, of an organism, typically a plant. With this aspect of the present invention the second construct does not cover the natural combination of the gene coding for an enzyme ordinarily associated with the wild type gene promoter when they are both in their natural environment.

An example of a suitable combination would be a first construct comprising the nucleotide sequence of the present invention and a promoter, such as the promoter of the present invention, and a second construct comprising a promoter, such as the promoter of the present invention, and a GOI wherein the GOI codes for another starch branching enzyme either in sense or antisense orientation.

The above comments relating to the term "construct" for the antisense nucleotide aspect of the present invention are equally applicable to the term "construct" for the promoter aspect of the present invention. In this regard, the term includes the promoter according to the present invention directly or indirectly attached to a GOI.

The term "GOI" with reference to the promoter aspect of the present invention or the combination aspect of the present invention means any gene of interest, which need not necessarily code for a protein or an enzyme—as is explained later. A GOI can be any nucleotide sequence that is either foreign or natural to the organism in question, for example a plant.

Typical examples of a GOI include genes encoding for other proteins or enzymes that modify metabolic and catabolic processes. The GOI may code for an agent for introducing or increasing pathogen resistance.

The GOI may even be an antisense construct for modifying the expression of natural transcripts present in the relevant tissues. An example of such a GOI is the nucleotide sequence according to the present invention.

The GOI may even code for a protein that is non-natural to the host organism—e.g. a plant. The GOI may code for a compound that is of benefit to animals or humans. For example, the GOI could code for a pharmaceutically active protein or enzyme such as any one of the therapeutic compounds insulin, interferon, human serum albumin, human growth factor and blood clotting factors. The GOI may even code for a protein giving additional nutritional value to a food or feed or crop. Typical examples include plant proteins that can inhibit the formation of anti-nutritive factors and plant proteins that have a more desirable amino acid composition (e.g. a higher lysine content than a non-transgenic plant). The GOI may even code for an enzyme that can be used in food processing such as xylanases and α-galactosidase. The GOI can be a gene encoding for any one of a pest toxin, an antisense transcript such as that for α-amylase, a protease or a glucanase. Alternatively, the GOI can be a nucleotide sequence according to the present invention.

The GOI can be the nucleotide sequence coding for the arabinofuranosidase enzyme which is the subject of our co-pending UK patent application 9505479.7. The GOI can be the nucleotide sequence coding for the glucanase enzyme which is the subject of our co-pending UK patent application 9505475.5. The GOI can be the nucleotide sequence coding for the a-amylase enzyme which is the subject of our co-pending UK patent application 9413439.2. The GOI can be the nucleotide sequence coding for the α-amylase enzyme which is the subject of our co-pending UK patent application 9421290.9. The GOI can be any of the nucleotide sequences coding for the α-glucan lyase enzyme which are described in our co-pending PCT patent application PCT/EP94103397.

In one aspect the GOI can even be a nucleotide sequence according to the present invention but when operatively linked to a different promoter.

The GOI could include a sequence that codes for one or more of a xylanase, an arabinase, an acetyl esterase, a rhamnogalacturonase, a glucanase, a pectinase, a branching enzyme or another carbohydrate modifying enzyme or proteinase. Alternatively, the GOI may be a sequence that is antisense to any of those sequences.

As mentioned above, the present invention provides a mechanism for selectively affecting a particular enzymatic activity. In an important application of the present invention it is now possible to reduce or eliminate expression of a genomic nucleotide sequence coding for a genomic protein or enzyme by expressing an antisense intron construct for that particular genomic protein or enzyme and (e.g. at the same time) expressing a recombinant version of that enzyme or protein—in other words the GOI is a recombinant nucleotide sequence coding for the genomic enzyme or protein. This application allows expression of desired recombinant enzymes and proteins in the absence of (or reduced levels of) respective genomic enzymes and proteins. Thus the desired recombinant enzymes and proteins can be easily separated and purified from the host, organism. This particular aspect of the present invention is very advantageous over the prior art methods which, for example, rely on the use of anti-sense exon expression which methods also affect expression of the recombinant enzyme.

Thus, a further aspect of the present invention relates to a method of expressing a recombinant protein or enzyme in a host organism comprising expressing a nucleotide sequence coding for the recombinant protein or enzyme; and expressing a further nucleotide sequence wherein the further nucleotide sequence codes, partially or completely, for an intron in an antisense orientation; wherein the intron is an intron normally associated with the genomic gene encoding a protein or an enzyme corresponding to the recombinant protein or enzyme; and wherein the further nucleotide sequence does not contain a sequence that is antisense to an exon sequence normally associated with the intron. Additional aspects cover the combination of those nucleotide sequences including their incorporation in constructs, vectors, cells, tissues and transgenic organisms.

Therefore the present invention also relates to a combination of nucleotide sequences comprising a first nucleotide sequence coding for a recombinant enzyme; and a second nucleotide sequence which corresponds to an intron in antisense orientation; wherein the intron is an intron that is associated with a genomic gene encoding an enzyme corresponding to the recombinant enzyme; and wherein the second nucleotide sequence does not contain a sequence that is antisense to an exon sequence normally associated with the intron.

The GOI may even code for one or more introns, such as any one or more of the intron sequences presented in the attached sequence listings. For example, the present invention also covers the expression of for example an antisense intron (e.g. SEQ.I.D.No. 15) in combination with for example a sense intron which preferably is not complementary to the antisense intron sequence (e.g. SEQ.I.D.No. 2).

The terms "cell", "tissue" and "organ" include cell, tissue and organ per se and when within an organism.

The term "organism" in relation to the present invention includes any organism that could comprise the nucleotide sequence according to the present invention and/or wherein the nucleotide sequence according to the present invention can be expressed when present in the organism. Preferably the organism is a starch producing organism such as any one of a plant, algae, fungi, yeast and bacteria, as well as cell lines thereof. Preferably the organism is a plant.

The term "starch producing organism" includes any organism that can biosynthesise starch. Preferably, the starch producing organism is a plant.

The term "plant" as used herein includes any suitable angiosperm, gymnosperm, monocotyledon and dicotyledon. Typical examples of suitable plants include vegetables such as potatoes; cereals such as wheat, maize, and barley; fruit; trees; flowers; and other plant crops. Preferably, the term means "potato".

The term "transgenic organism" in relation to the present invention includes any organism that comprises the nucleotide sequence according to the present invention and/or products obtained therefrom, and/or wherein the nucleotide sequence according to the present invention can be expressed within the organism. Preferably the nucleotide sequence of the present invention is incorporated in the genome of the organism. Preferably the transgenic organism is a plant, more preferably a potato.

To prepare the host organism one can use prokaryotic or eukaryotic organisms. Examples of suitable prokaryotic hosts include *E. coli* and *Bacillus subtilis*. Teachings on the transformation of prokaryotic hosts is well documented in the art, for example see Sambrook et al (Sambrook et al. in Molecular Cloning: A Laboratory Manual, 2nd edition, 1989, Cold Spring Harbor Laboratory Press).

Even though the enzyme according to the present invention and the nucleotide sequence coding for same are not disclosed in EP-B-0470145 and CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 17–27, 1994).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists,* eds.: D. S. Ingrams and J. P. Helgeson, 203–208. Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appears to be essential for insertion of modified T-DNA into the plant genome.

As will be understood from the above explanation, if the organism is a plant the vector system of the present invention is preferably one which contains the sequences necessary to infect the plant (e.g. the vir region) and at least one border part of a T-DNA sequence, the border part being located on the same vector as the genetic construct.

Furthermore, the vector system is preferably an *Agrobacterium tumefaciens* Ti-plasmid or an *Agrobacterium rhizogenes* Ri-plasmid or a derivative thereof. As these plasmids are well-known and widely employed in the construction of transgenic plants, many vector systems exist which are based on these plasmids or derivatives thereof.

In the construction of a transgenic plant the nucleotide sequence or construct of the present invention may be first constructed in a microorganism in which the vector can replicate and which is easy to manipulate before insertion into the plant. An example of a useful microorganism is *E. coli,* but other microorganisms having the above properties may be used. When a vector of a vector system as defined above has been constructed in *E. coli,* it is transferred, if necessary, into a suitable Agrobacterium strain, e.g. *Agrobacterium tumefaciens.* The Ti-plasmid harbouring the nucleotide sequence or construct of the present invention is thus preferably transferred into a suitable Agrobacterium strain, e.g. A. tumefaciens, so as to obtain an Agrobacterium cell harbouring the promoter or nucleotide sequence or construct of the present invention, which DNA is subsequently transferred into the plant cell to be modified.

If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980), *Tissue Culture Methods for Plant Pathologists,* eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 17–27, 1994). With this technique, infection of a plant may be performed in or on a certain part or tissue of the plant, i.e. on a part of a leaf, a root, a stem or another part of the plant.

Typically, with direct infection of plant tissues by Agrobacterium carrying the GOI (such as the nucleotide sequence according to the present invention) and, optionally, a promoter, a plant to be infected is wounded, e.g. by cutting the plant with a razor blade or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc.

Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

As reported in CA-A-2006454, a large amount of cloning vectors are available which contain a replication system in *E. coli* and a marker which allows a selection of the transformed cells. The vectors contain for example pBR 322, pUC series, M13 mp series, pACYC 184 etc. In this way, the nucleotide or construct of the present invention can be introduced into a suitable restriction position in the vector. The contained plasmid is then used for the transformation in *E. coli.* The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After the introduction of the nucleotide sequence or construct according to the present invention in the plants the presence and/or insertion of further DNA sequences may be necessary—such as to create combination systems as outlined above (e.g. an organism comprising a combination of constructs).

The above commentary for the transformation of procaryotic organisms and plants with the nucleotide sequence of the present invention is equally applicable for the transformation of those organisms with the promoter of the present invention.

In summation, the present invention relates to affecting enzyme activity by expressing antisense intron sequences.

Also, the present invention relates to a promoter useful for the expression of those antisense intron sequences.

The following samples have been deposited in accordance with the Budapest Treaty at the recognised depository The National Collections of Industrial and Marine Bacteria Limited (NCIMB) at 23 St Machar Drive, Aberdeen, Scotland, AB2 1RY, United Kingdom, on Jul. 13, 1995:

NCIMB 40753 (which refers to pBEA 8 as described herein);

NCIMB 40751 (which refers to λ-SBE 3.2 as described herein), and

NCIMB 40752 (which refers to λ-SBE 3.4 as described herein).

The following sample has been deposited in accordance with the Budapest Treaty at the recognised depository The National Collections of Industrial and Marine Bacteria Limited (NCIMB) at 23 St Machar Drive, Aberdeen, Scotland, AB2 1RY, United Kingdom, on Jul. 9, 1996:
NCIMB 40815 (which refers to pBEA 9 as described herein).

A highly preferred embodiment of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in an antisense orientation; wherein the nucleotide sequence does not contain a sequence that is antisense to an exon sequence normally associated with the intron; wherein starch branching enzyme activity is affected and/or the levels of amylopectin are affected and/or the composition of starch is changed; and wherein the nucleotide sequence is obtainable from NCIMB 40753 or NCIMB 40815, or is antisense to any one or more of the intron sequences obtainable from either λ-SBE 3.2 (NCIMB 40751) or λSBE 3.4 (NCIMR 40752) or a variant, derivative or homologue thereof.

A more highly preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in an antisense orientation; wherein the nucleotide sequence does not contain a sequence that is antisense to an exon sequence normally associated with the intron; wherein starch branching enzyme activity is affected and/or the levels of amylopectin are affected and/or the composition of starch is changed; wherein the nucleotide sequence comprises the sequence shown as any one of SEQ.I.D. No. 15 to SEQ.I.D. No. 27 or a variant, derivative or homologue thereof, including combinations thereof; and wherein the nucleotide sequence is obtainable from NCIMB 40753 or NCIMB 40815, or is antisense to any one or more of the intron sequences obtainable from either λSBE 3.2 (NCIMB 40751) or λSBE 3.4 (NCIMB 40752) or a variant, derivative or homologue thereof.

BRIEF DESCRIPTION OF THE DRAWINGS

FIG. 12, which shows the full genomic nucleotide sequence for SBE including the promoter, exons and introns.

DETAILED DESCRIPTION OF THE INVENTION

Figure 1:
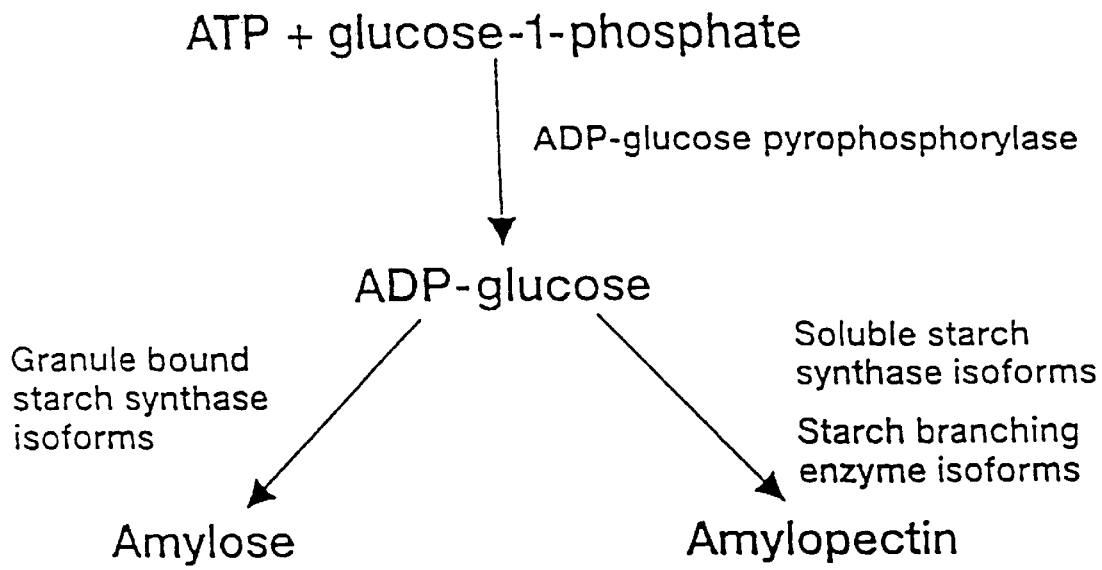
FIG. 1, which is a schematic representation of the biosynthesis of amylose and amylopectin.
Figure 1:
Figure 1:
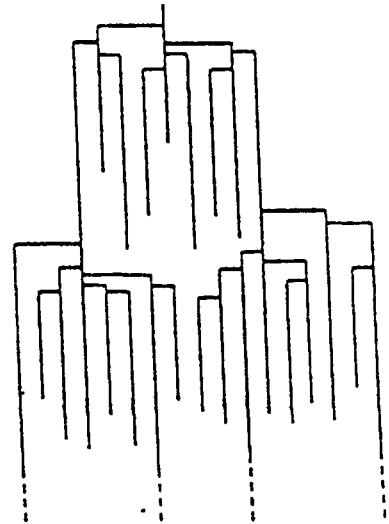
Figure 2:
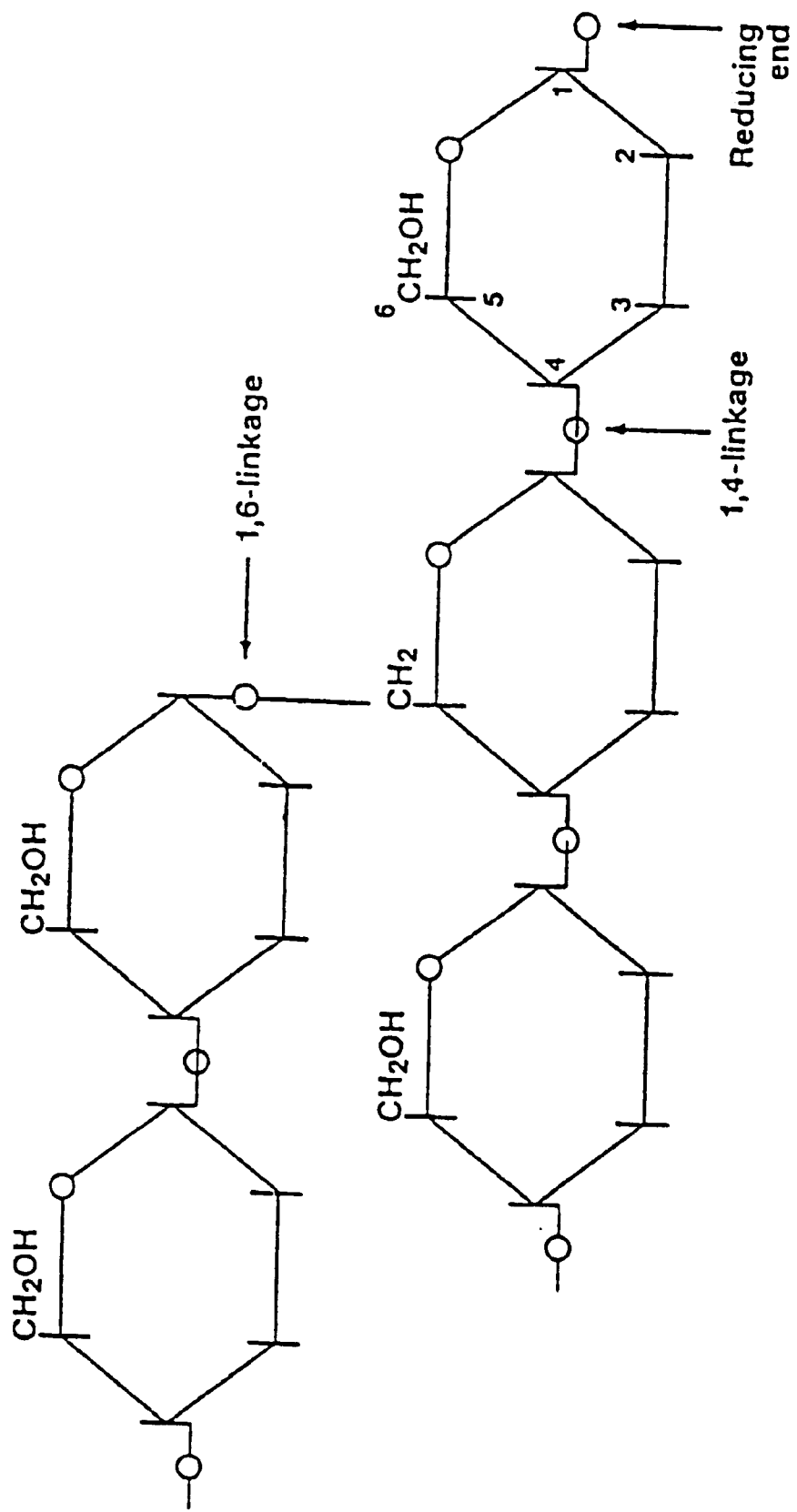
FIG. 2, which is a diagrammatic representation of the α-1-4-links and the α-1-6 links of amylopectin.
Figure 3:
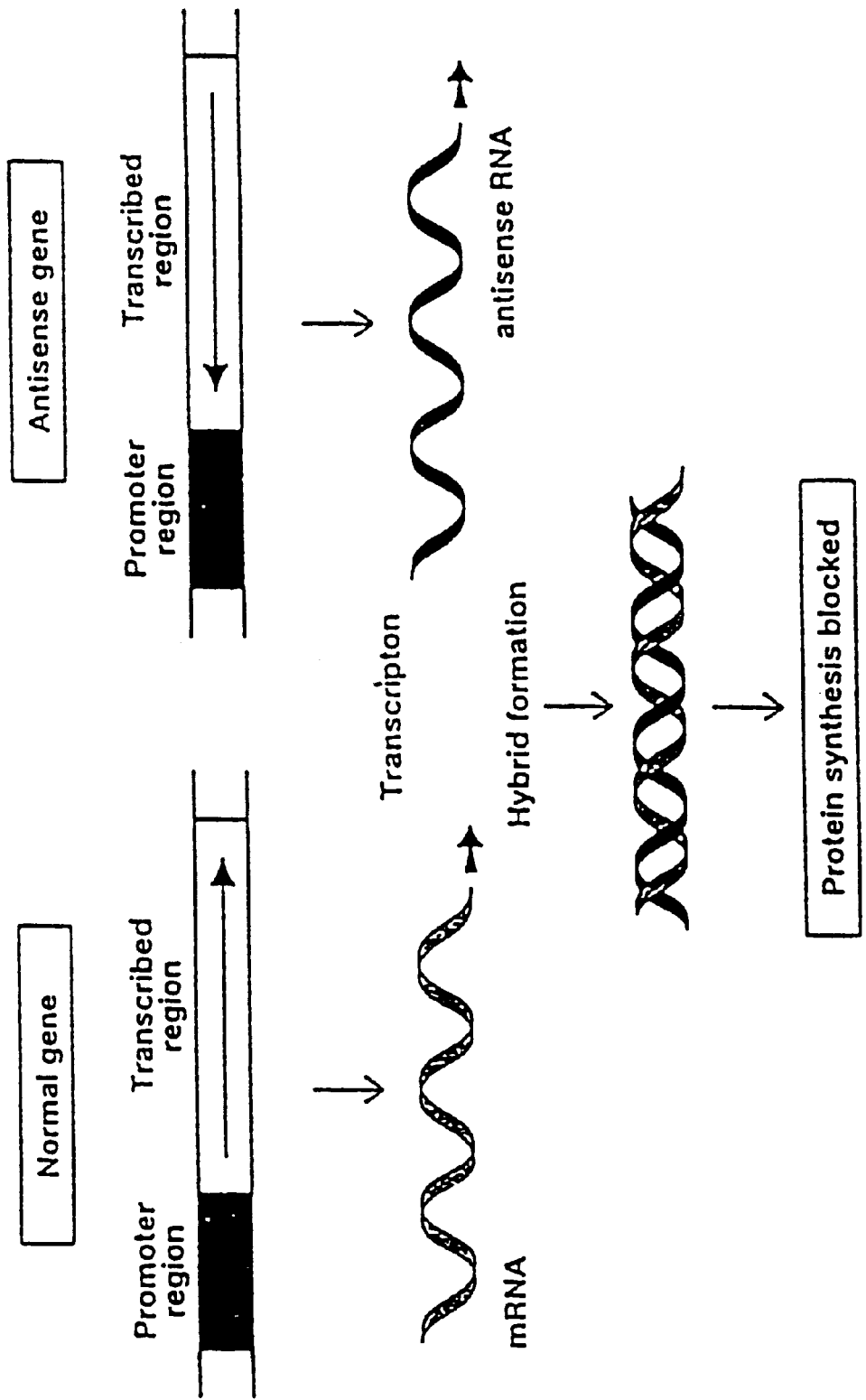
FIG. 3, which is a diagrammatic representation of a possible antisense-RNA inhibition mechanism.

FIGS. 1 and 2 were referred to above in the introductory description concerning starch in general. FIG. 3 was referred to above in the introductory description concerning antisense expression.

Figure 4:
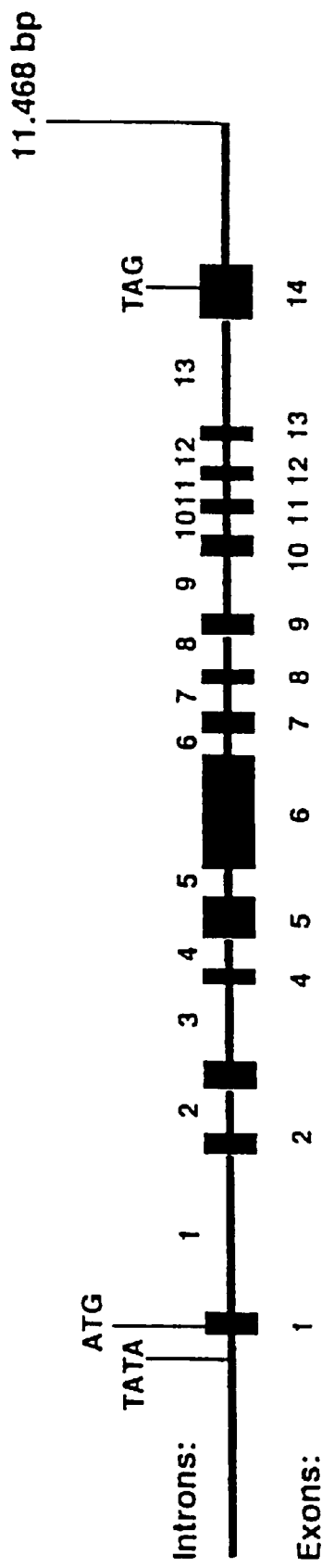
FIG. 4, which is a diagrammatic representation of the exon-intron structure of a genomic SBE clone.

As mentioned, FIG. 4 is a diagrammatic representation of the exon-intron structure of a genomic SBE clone, the sequence of which is shown in FIG. 12. This clone, which has about 11.5 k base pairs, comprises 14 exons and 13 introns. The introns are numbered in increasing order from the 5' end to the 3' end and correspond to SEQ.I.D.No.s 1–13, respectively. Their respective antisense intron sequences are shown as SEQ.I.D.No.s 15–27.

In more detail, FIGS. 4 and 12 present information on the 11478 base pairs of a potato SBE gene. The 5' region from nucleotides 1 to 2082 contain the promoter region of the SBE gene. A TATA box candidate at nucleotide 2048 to 2051 is boxed. The homology between a potato SBE cDNA clone (Poulsen & Kreiberg (1993) Plant Physiol 102: 1053–1054) and the exon DNAs begin at 2083 bp and end at 9666 bp. The homology between the cDNA and the exon DNA is indicated by nucleotides in upper case letters, while the translated amino acid sequences are shown in the single letter code below the exon DNA. Intron sequences are indicated by lower case letters.

Figure 5:
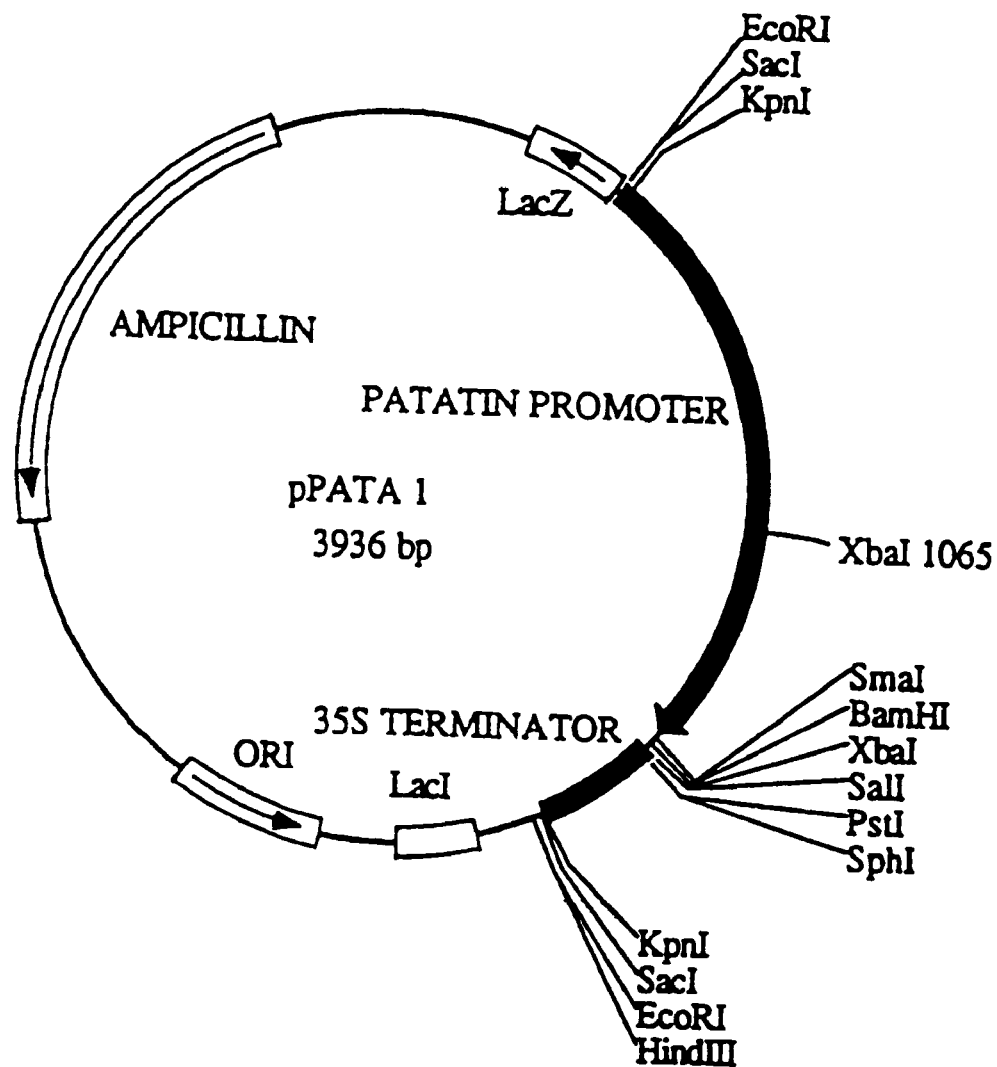
FIG. 5, which is a plasmid map of pPATA1, which is 3936 bp in size.
Figure 6:
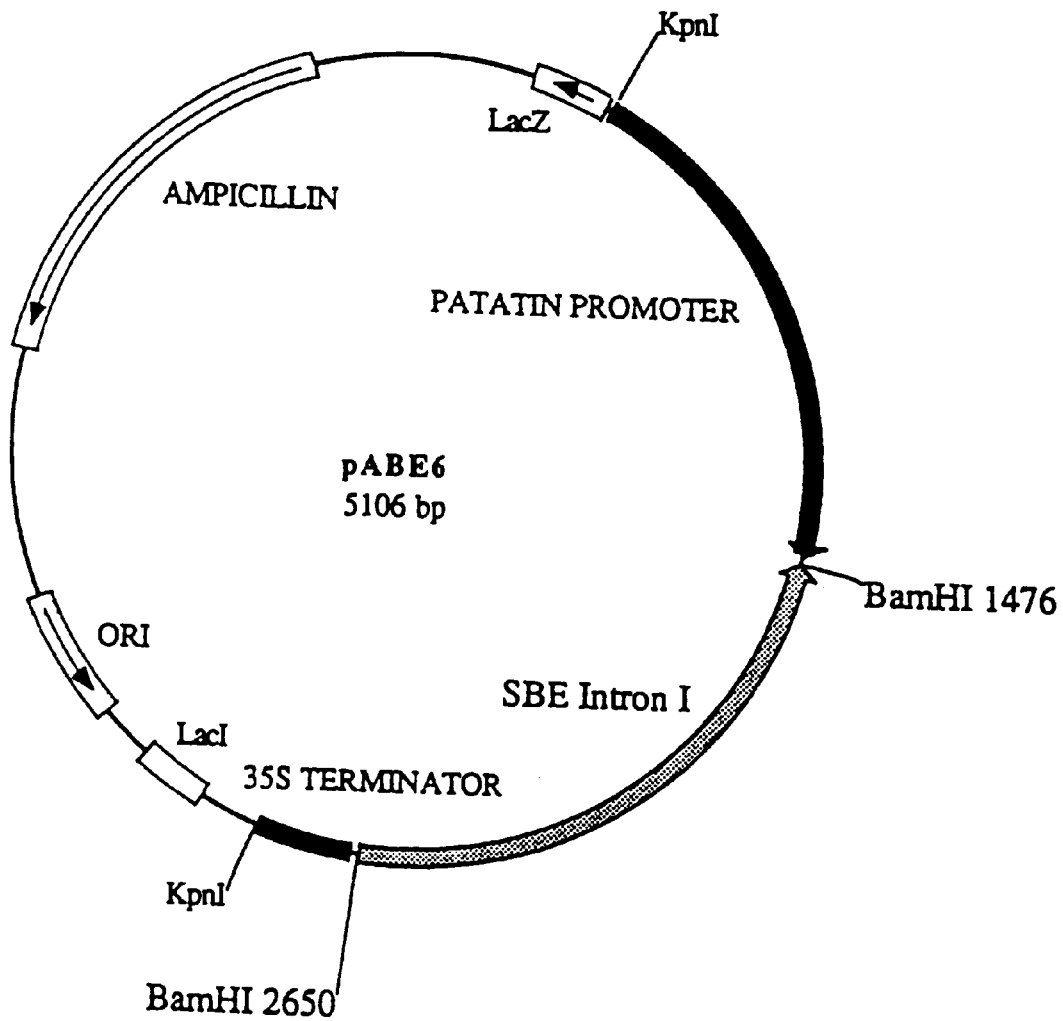
FIG. 6, which is a plasmid map of pABE6, which is 5106 bp in size.
Figure 7:
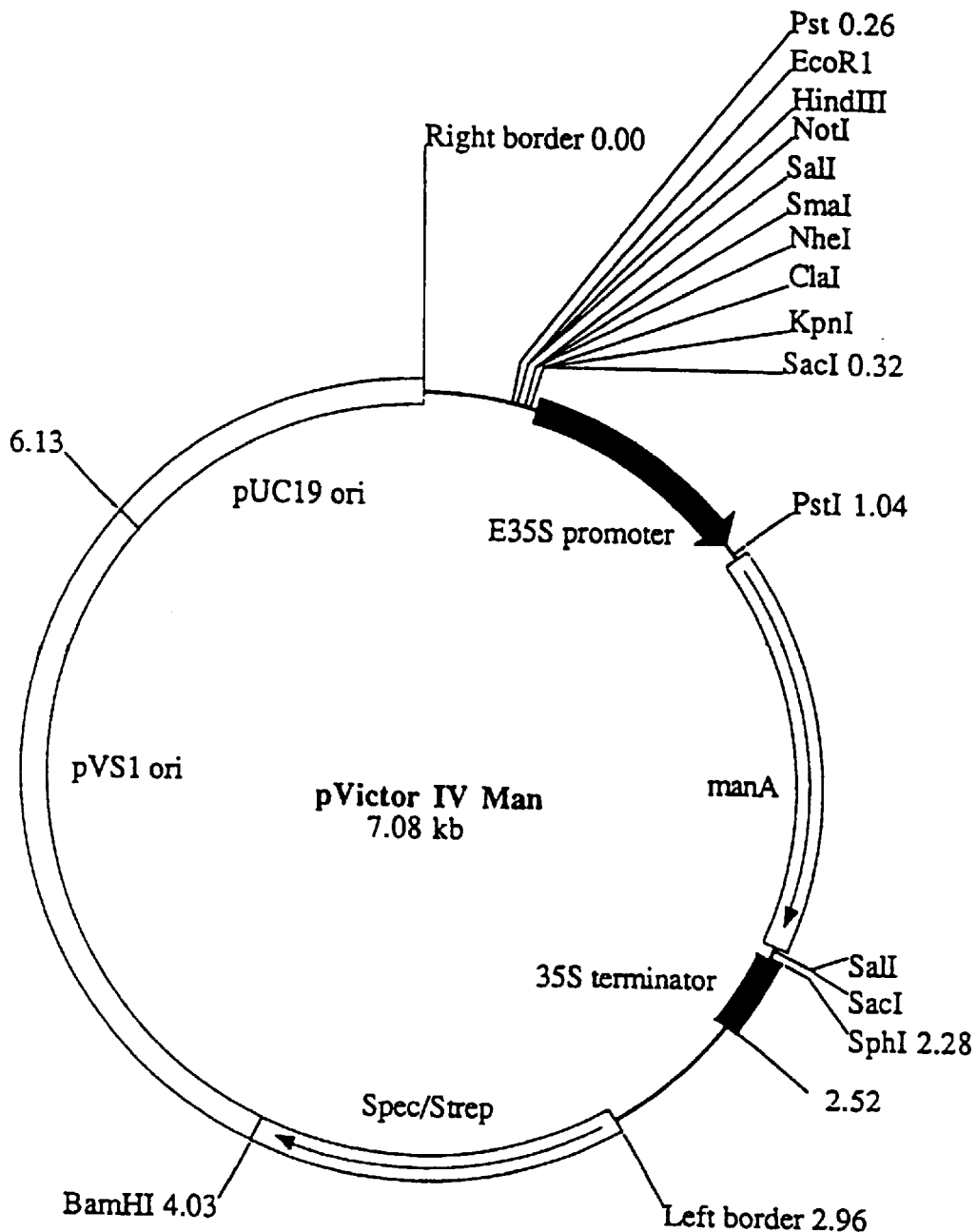
FIG. 7, which is a plasmid map of pVictorIV Man, which is 7080 bp in size.
Figure 8:
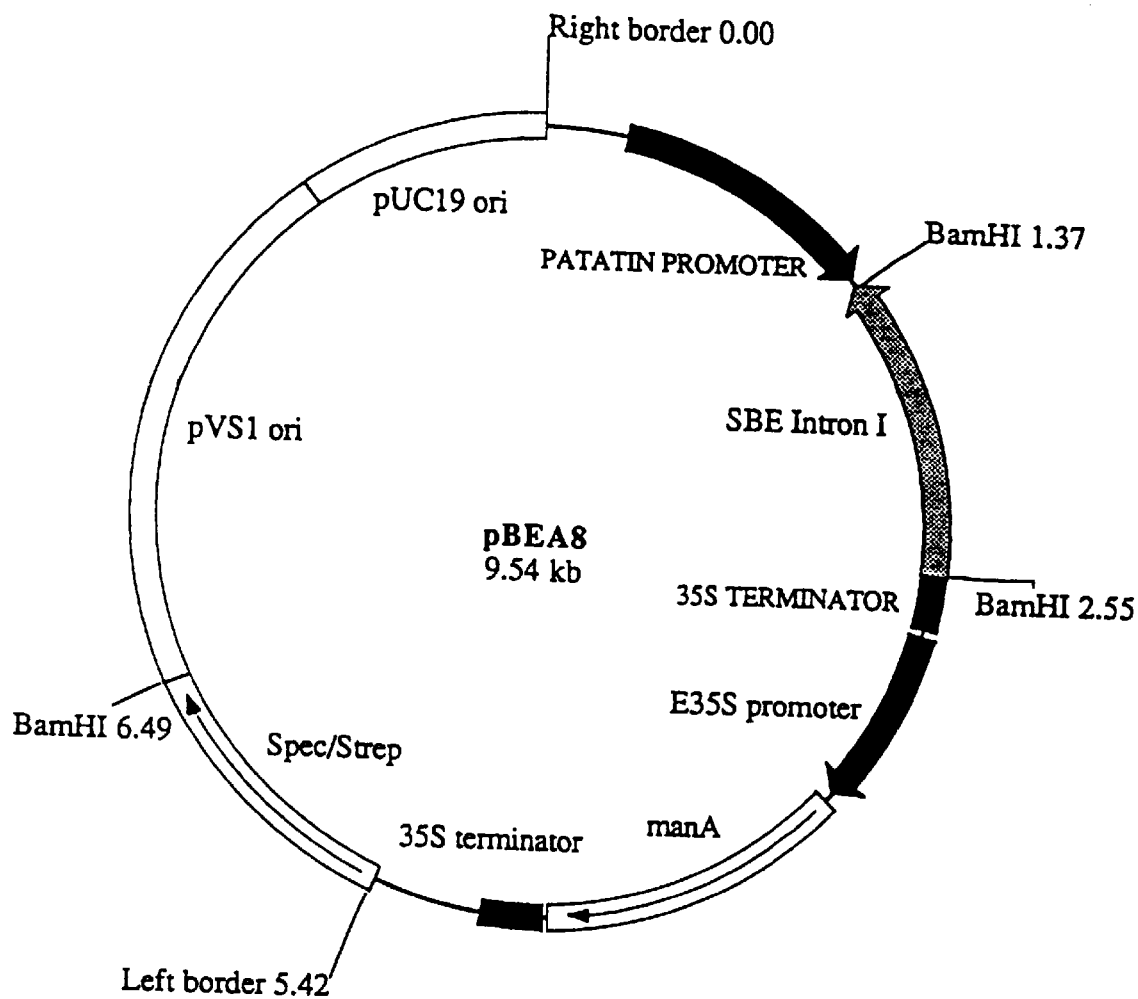
FIG. 8, which is a plasmid map of pBEA8, which is 9.54 kb in size.
Figure 9:
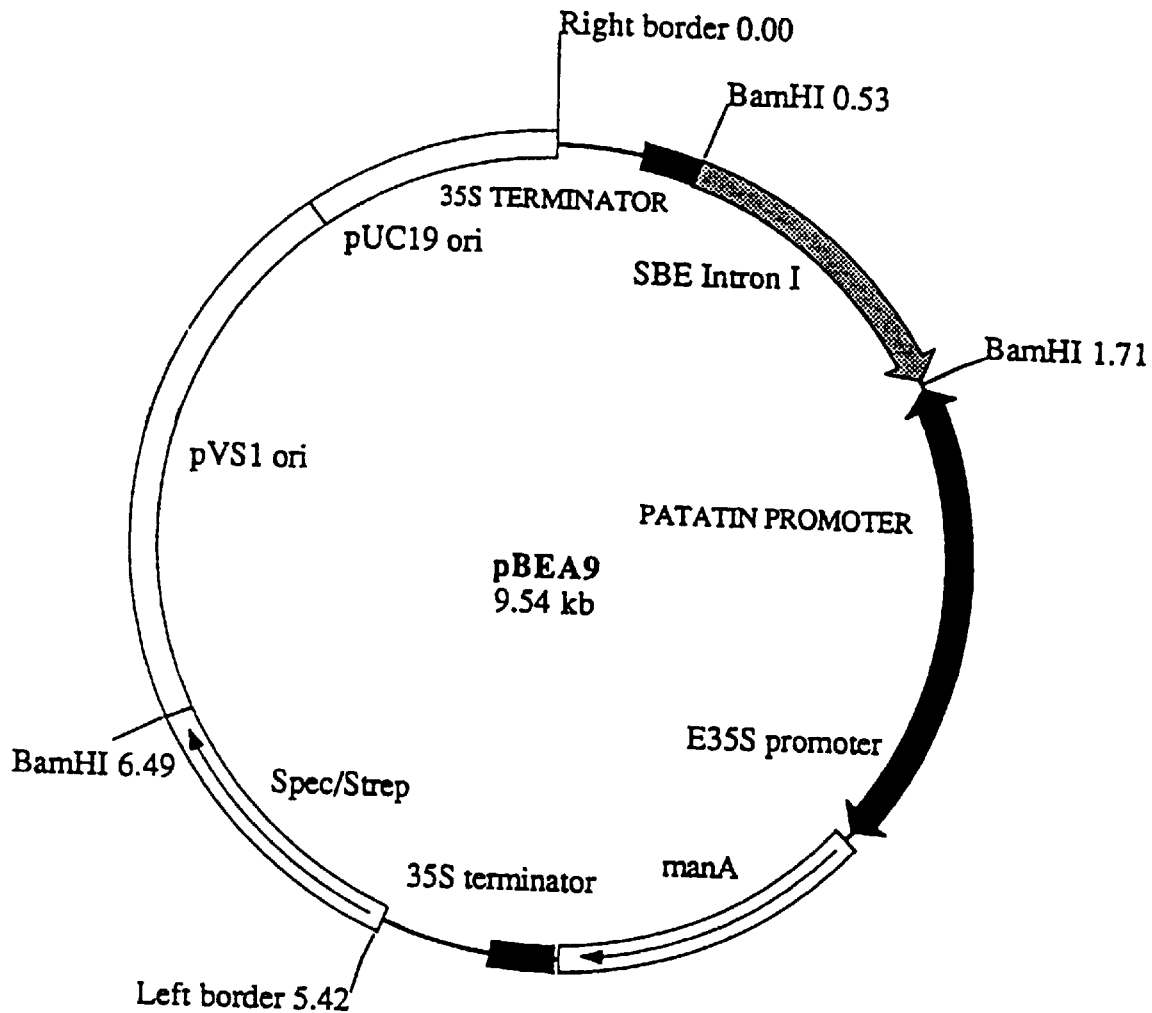
FIG. 9, which is a plasmid map of pBEA9, which is 9.54 kb in size.

FIGS. 5 to 7 are discussed below. As mentioned, FIG. 8 is a plasmid map of pBEA8, which is 9.54 k base pairs in size; and FIG. 9 is a plasmid map of pBEA9, which is 9.54 k base pairs in size. Each of pBEA 8 and pBEA 9 comprises an antisense sequence to the first intron sequence of the potato SBE gene. This first intron sequence, which has 1177 base pairs, is shown in FIG. 4 and lies between the first exon and the second exon.

These experiments and aspects of the present invention are now discussed in more detail.

Experimental Protocol

Isolation, Subcloning in Plasmas, and Sequencing of Genomic SBE Clones

Various clones containing the potato SBE gene were isolated from a Desiree potato genomic library (Clontech Laboratories Inc., Palo Alto Calif., USA) using radioactively labelled potato SBE cDNA (Poulsen & Kreiberg (1993) Plant Physiol. 102:1053–1054) as probe. The fragments of the isolated λ-phages containing SBE DNA (λSBE 3.2-NCIMB 40751- and λSBE-3.4-NCIMB 40752) were identified by Southern analysis and then subcloned into pBluescript II vectors (Clontech Laboratories Inc., Palo Alto Calif., USA). λSBE 3.2 contains a 15 kb potato DNA insert and λSBE-3.4 contains a 13 kb potato DNA insert. The resultant plasmids were called pGB3, pGB11, pGB15, pGB16 and pGB25 (see discussion below). The respective inserts were then sequenced using the Pharmacia Autoread Sequencing Kit (Pharmacia, Uppsala) and a A.L.F. DNA sequencer (Pharmacia, Uppsala).

In total, a stretch of 11.5 kb of the SBE gene was sequenced. The sequence was deduced from the above-mentioned plasmids, wherein: pGB25 contains the sequences from 1 bp to 836 bp, pGB15 contains the sequences from 735 bp to 2580 bp, pGB16 contains the sequences from 2580 bp to 5093 bp, pGB11 contains the sequences from 348 bp to 7975 bp, and pGB3 contains the sequences from 7533 bp to 11468 bp.

In more detail, pGB3 was constructed by insertion of a 4 kb EcoRI fragment isolated from λSBE 3.2 into the EcoRI site of pBluescript II SK (+). pGB11 was constructed by insertion of a 4.7 kb XhoI fragment isolated from λSBE 3.4 into the XhoI site of pBluescript II SK (+). pGB15 was constructed by insertion of a 1.7 kb SpeI fragment isolated from λSBE 3.4 into the SpeI site of pBluescript II SK (+). pGB16 was constructed by insertion of a 2.5 kb SpeI fragment isolated from λSBE 3.4 into the SpeI site of pBluescript II SK (+). For the construction of pGB25 a PCR fragment was produced with the primers 5' GGA ATT CCA GTC GCA GTC TAC ATT AC 3' (SEQ ID NO. 30) and 5' CGG GAT CCA GAG GCA TTA AGA TTT CTG G 3' (SEQ ID NO. 31) and λSBE 3.4 as a template.

The PCR fragment was digested with BamHI and EcoRI, and inserted in pBluescript II SK (+) digested with the same restriction enzymes.

Construction of SBE Antisense Intron Plasmids pBEA8 and pBEA9

The SBE intron 1 was amplified by PCR using the oligonucleotides:

5' CGG GAT CCA AAG AAA TTC TCG AGG TTA CAT GG 3' (SEQ ID NO. 32) and

5' CGG GAT CCG GGG TAA TTT TTA CTA ATT TCA TG 3' (SEQ ID NO. 33) and the λSBE 3.4 phage containing the SBE gene as template.

The PCR product was digested with BamHI and inserted in an antisense orientation in the BamHI site of plasmid pPATA1 (described in WO 94/24292) between the patatin promoter and the 35S terminator. This construction, pABE6, was digested with KpnI, and the 2.4 kb "patatin promoter-SBE intron 1-35S terminator" KpnI fragment was isolated and inserted in the KpnI site of the plant transformation vector pVictorIV Man. The KpnI fragment was inserted in two orientations yielding plasmids pBEA8 and pBEA9. pVictorIV Man is shown in FIG. 7 and is formed by insertion of a filled in XbaI fragment containing a E35S promoter-manA-35S terminator cassette, isolated from plasmid pVictorIV SGiN Man (WO 94/24292) into the filled in XhoI site of pVictor IV. The pVictor regions of pVictor IV Man contained between the coordinates 2.52 bp to 0.32 bp (see FIG. 7).

Production of Transgenic Potato Plants

Axenic stock cultures

Shoot cultures of *Solanum tuberosum* 'Bintje' and 'Dianella' are maintained on a substrate (LS) of a formula according to Linsmaier, E. U. and Skoog, F. (1965), Physiol. Plant. 18: 100–127, in addition containing 2 μM silver thiosulphate at 25° C. and 16 h light/8 h dark.

The cultures were subcultured after approximately 40 days. Leaves were then cut off the shoots and cut into nodal segments (approximately 0.8 cm) each containing one node.

Inoculation of potato tissues

Shoots from approximately 40 days old shoot cultures (height approximately 5–6 cms) were cut into internodal segments (approximately 0.8 cm). The segments were placed into liquid LS-substrate containing the transformed *Agrobacterium tumefaciens* containing the binary vector of interest. The Agrobacterium were grown overnight in YMB-substrate (di-potassium hydrogen phosphate, trihydrate (0.66 g/l); magnesium sulphate, heptahydrate (0.20 g/l); sodium chloride (0.10 g/l); mannitol (10.0 g/l); and yeast extract (0.40 g/l)) containing appropriate antibiotics (corresponding to the resistance gene of the Agrobacterium strain) to an optical density at 660 nm (OD-660) of approximately 0.8, centrifuged and resuspended in the LS-substrate to an OD-660 of 0.5.

The segments were left in the suspension of Agrobacterium for 30 minutes and then the excess of bacteria were removed by blotting the segments on sterile filter paper.

Co-cultivation

The shoot segments were co-cultured with bacteria for 48 hours directly on LS-substrate containing agar (8.0 g/l), 2,4-dichlorophenoxyacetic acid (2.0 mg/l) and trans-zeatin (0.5 mg/l). The substrate and also the explants were covered with sterile filter papers, and the petri dishes were placed at 25° C. and 16 h light/8 dark.

"Washing" procedure

After the 48 h on the co-cultivation substrate the segments were transferred to containers containing liquid LS-substrate containing 800 mg/l carbenicillin. The containers were gently shaken and by this procedure the major part of the Agrobacterium was either washed off the segments and/or killed.

Selection

After the washing procedure the segments were transferred to plates containing the LS-substrate, agar (8 g/l), trans-zeatin (1–5 mg/l), gibberellic acid (0.1 mg/l), carbenicillin (800 mg/l), and kanamycin sulphate (50–100 mg/l) or phosphinotricin (1–5 mg/l) or mannose (5 g/l) depending on the vector construction used.

The segments were sub-cultured to fresh substrate each 34 weeks.

In 3 to 4 weeks, shoots develop from the segments and the formation of new shoots continued for 34 months.

Rooting of regenerated shoots

The regenerated shoots were transferred to rooting substrate composed of LS-substrates agar-(8 g/l) and carbenicillin (800 mg/l).

The transgenic genotype of the regenerated shoot was verified by testing the rooting ability on the above mentioned substrates containing kanamycin sulphate (200 mg/l), by performing NPTII assays (Radke, S. E. et al, Theor. Appl. Genet. (1988), 75: 685–694) or by performing PCR analysis according to Wang et al (1993, NAR 21 pp 4153–4154). Plants which were not positive in any of these assays were discarded or used as controls. Alternatively, the transgenic plants could be verified by performing a GUS assay on the co-introduced fi-glucuronidase gene according to Hodal, L. et al. (Pl. Sci. (1992), 87: 115–122).

Transfer to soil

The newly rooted plants (height approx. 2–3 cms) were transplanted from rooting substrate to soil and placed in a growth chamber (21° C., 16 hour light 200–400 uE/m²/sec). When the plants were well established they were transferred to the greenhouse, where they were grown until tubers had developed and the upper part of the plants were senescing.

Harvesting

The potatoes were harvested after about 3 months and then analysed.

Branching Enzyme Analysis

The SBE expression in the transgenic potato lines were measured using the SBE assays described by Blennow and Johansson (Phytochemistry (1991) 30:437–444) and by standard Western procedures using antibodies directed against potato SBE.

Starch Analysis

Starch was isolated from potato tubers and analysed for the amylose:amylopectin ratio (Hovenkamp-Hermelink et al. (1988) Potato Research 31:241–246). In addition, the chain length distribution of amylopectin was determined by analysis of isoamylase digested starch on a Dionex HPAEC.

The number of reducing ends in isoamylase digested starch was determined by the method described by N. Nelson (1944) J. Biol.Chem. 153:375–380.

The results revealed that there was a reduction in the level of synthesis of SBE and/or the level of activity of SBE and/or the composition of starch SBE in the transgenic plants.

Construction of SBE Promoter Construct

An SBE promoter fragment was amplified from λ-SBE 3.4 using primers:
5' CCA TCG ATA CTT TAA GTG ATT TGA TGG C 3' and
5' CGG GAT CCT GTT CTG ATT CTT GAT TTC C 3'.

Figure 10:
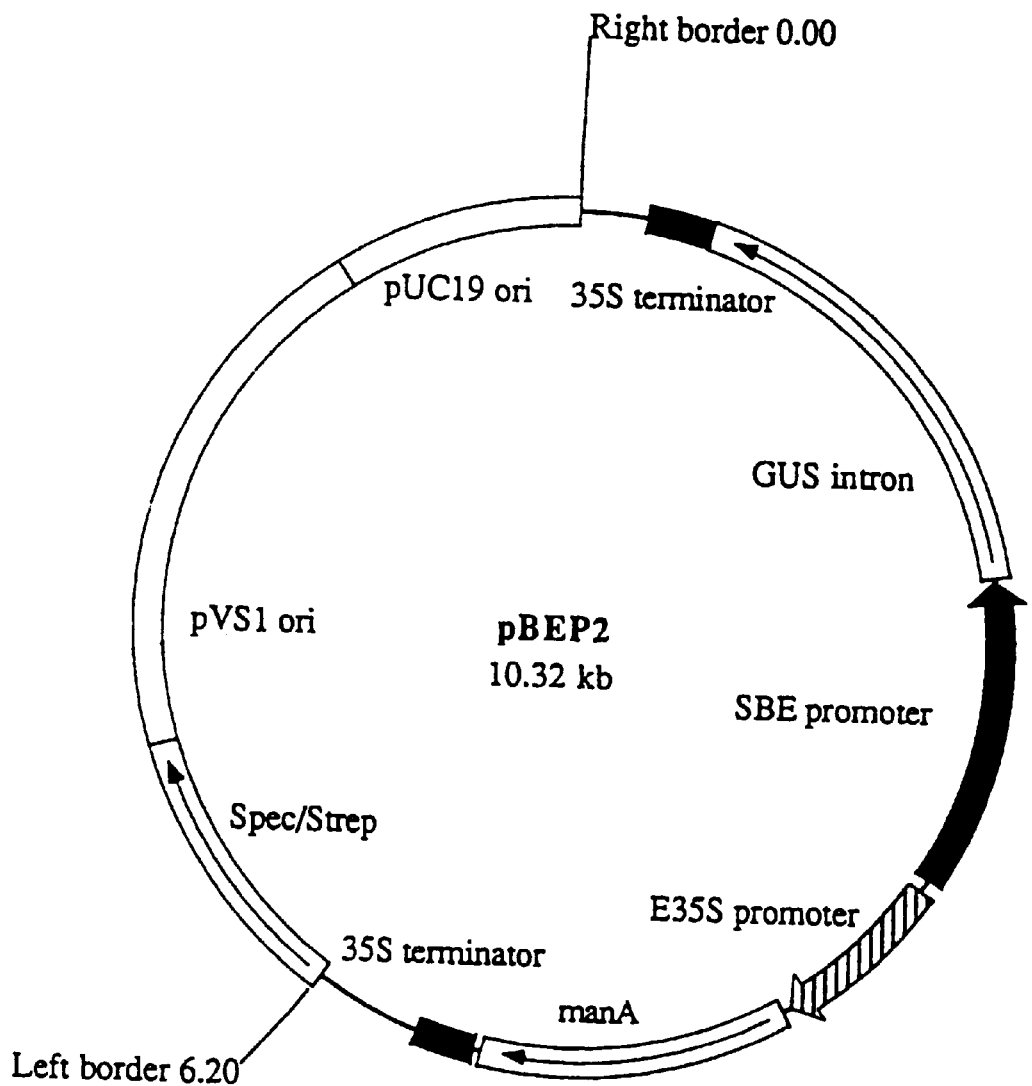
FIG. 10, which is a plasmid map of pBEP2, which is 10.32 kb in size.
Figure 11:
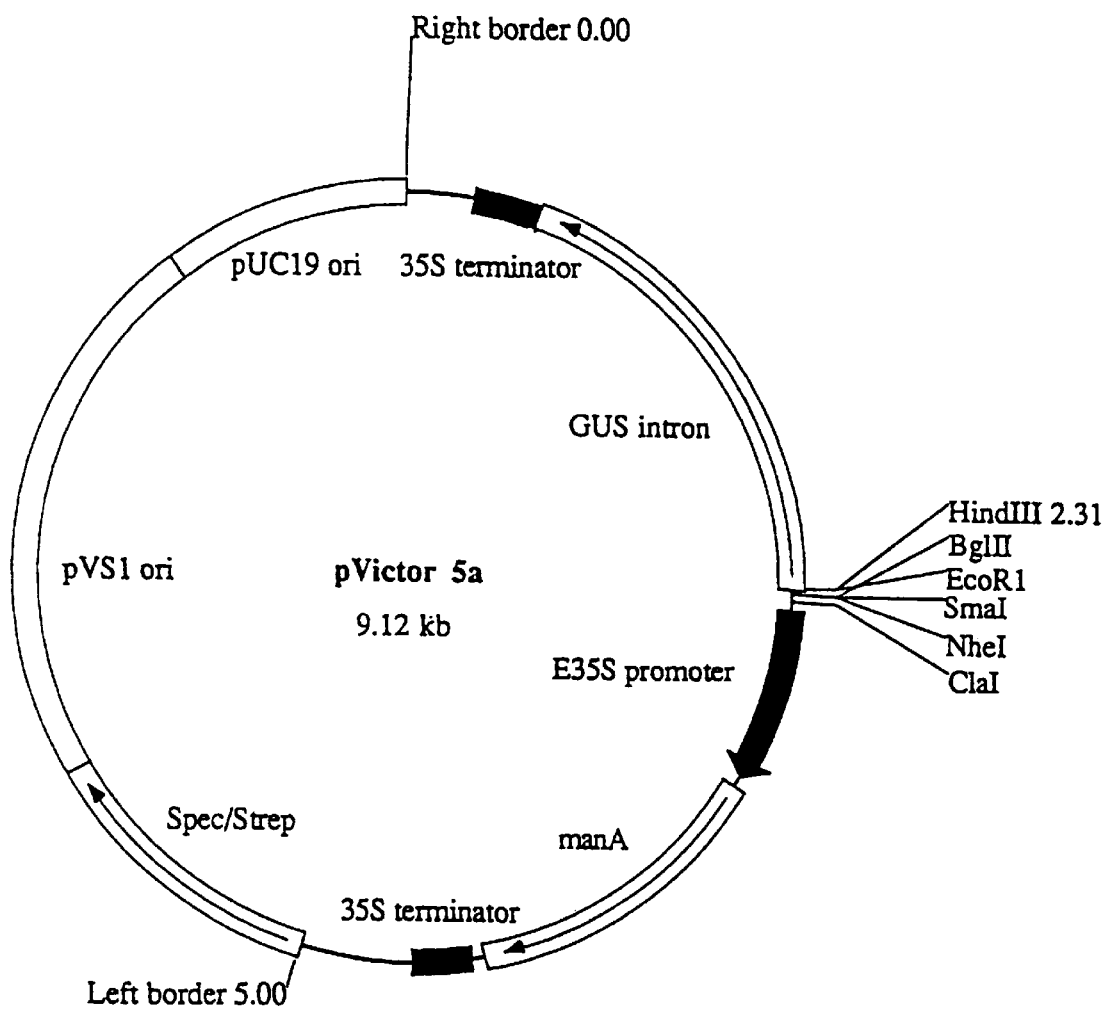
FIG. 11, which is a plasmid map of pVictor5a, which is 9.12 kb in size.

The PCR product was digested with ClaI and BamHI. The resultant 1.2 kb fragment was then inserted in pVictor5a (see FIG. 11) linearised with ClaI and BglII yielding pBEP2 (see FIG. 10).

Starch Branching Enzyme Measurements of Potato Tubers

Potatoes from potato plants transformed with either pBEA8 or pBEA9 were cut in small pieces and homogenised in extraction buffer (50 mM Tris-HCl pH 7.5, Sodium-dithionit (0.1 g/l), and 2 mM DTT) using a Ultra-Turax homogenizer; 1 g of Dowex x1. was added pr. 10 g of tuber. The crude homogenate was filtered through a miracloth filter and centrifuged at 4° C. for 10 minutes at 24.700 g. The supernatant was used for starch branching enzyme assays.

The starch branching enzyme assays were carried out at 25° C. in a volume of 400 μl composed of 0.1 M Na citrate buffer pH 7.0, 0.75 mg/ml amylose, 5 mg/ml bovine serum albumin and the potato extract. At 0, 15, 30 and 60 minutes aliqouts of 50 μl were removed from the reaction into 20 μl 3 N HCl. 1 ml of iodine solution was added and the decrease in absorbance at 620 nm was measured with an ELISA spectrophotometer.

The starch branching enzyme (SBE) levels were measured in tuber extracts from 34 transgenic Dianella potato plants transformed with plasmid pBEA9.

The BEA9 transformed transgenic lines produced tubers which have SBE levels that are 10% to 15% of the SBE levels found in non transformed Dianella plants.

Summation

The above-mentioned examples relate to the isolation and sequencing of a gene for potato SBE. The examples further demonstrate that it is possible to prepare SBE intron antisense constructs. These SBE intron antisense constructs can be introduced into plants, such as potato plants. After introduction, a reduction in the level of synthesis of SBE and/or the level of activity of SBE and/or the composition of starch in plants can be achieved.

Without wishing to be bound by theory it is believed that the expressed anti-sense nucleotide sequence of the present invention binds to sense introns on pre-mRNA and thereby prevents pre-mRNA splicing and/or subsequent translation of mRNA. This binding therefore is believed to reduce the level of plant enzyme activity (in particular SBE activity), which in turn for SBE activity is believed to influence the amylose:amylopectin ratio and thus the branching pattern of amylopectin.

Thus, the present invention provides a method wherein it is possible to manipulate the starch composition in plants, or tissues or cells thereof, such as potato tubers, by reducing the level of SBE activity by using an antisense-RNA technique using antisense intron sequences.

In summation the present invention therefore relates to the surprising use of antisense intron sequences in a method to affect enzymatic activity in plants.

Other modifications of the present invention will be apparent to those skilled in the art without departing from the scope of the present invention.

For example, it may be possible to use antisense promoter sequences to affect enzymatic activity, such as antisense SBE promoter—such as a nucleotide sequence comprising the nucleotide sequence shown as SEQ. I.D. No. 28 or a variant, derivative or homologue thereof.

The following pages present a number of sequence listings which have been consecutively numbered from SEQ.I.D. No. 1–SEQ.I.D. No. 29. In brief, SEQ.I.D. No. 1–SEQ.I.D. No. 13 represent sense intron sequences (genomic DNA); SEQ.I.D. No. 14 represents the SBE promoter sequence (genomic sequence); SEQ.I.D. No. 15–SEQ.I.D. No. 27 represent antisense intron sequences: and SEQ. I.D. No. 28 represents is the sequence complementary to the SBE promoter sequence i.e. the SBE promoter sequence in antisense orientation. The full genomic nucleotide sequence for SBE including the promoter, exons and introns is shown as SEQ. I.D. No. 29 and is explained by way of FIGS. 4 and 12 which highlight particular gene features.

What is claimed is:

1. A method of reducing the activity of a potato starch branching enzyme in a plant or a cell, a tissue or an organ thereof comprising expressing in the plant, or the cell, the tissue or the organ thereof, a nucleic acid molecule encoding antisense RNA to an intron associated with a genomic sequence encoding said enzyme; wherein the nucleic acid molecule does not encode antisense RNA to an exon of the genomic sequence.

2. The method of claim 1 wherein the levels of amylopectin are reduced or the composition of starch is changed.

3. The method according to claim 1 wherein the nucleic acid molecule encodes an antisense RNA to intron 1 of potato starch branching enzyme.

4. The method according to claim 1 wherein the nucleic acid molecule comprises the sequence shown as ally one of SEQ. ID. No. 15 to SEQ. ID. No. 27.

5. The method according to claim 1 wherein the nucleic acid molecule is expressed by a promoter having a sequence comprising the sequence shown as SEQ. ID. No. 14.

6. The method according to claim 3 wherein the nucleic acid molecule is expressed by a promoter having a sequence comprising the sequence shown as SEQ. ID. No. 14.

7. An isolated nucleic acid molecule comprising the nucleotide sequence shown as any one of SEQ. ID. No. 15 to SEQ. ID. No. 27.

8. A vector comprising the nucleic acid molecule according to claim 7.

9. A transgenic plant comprising an isolated nucleic acid molecule encoding antisense RNA to an intron associated with a genomic sequence encoding a potato starch branching enzyme normally expressed by the cell, the tissue or the organ; wherein the nucleic acid molecule does not encode antisense RNA to an exon of the genomic sequence.

10. A transgenic plant comprising an isolated nucleic acid molecule according to claim 7.

11. pBEA8 (NCIMB 40753) or pBEA9 (NICMB 40815).

12. A method of expressing a potato starch branching enzyme in a plant comprising expressing a first nucleic acid molecule coding for the potato starch branching enzyme; and expressing a second nucleic acid molecule; wherein second nucleic acid molecule encodes an antisense RNA to an intron associated with a genomic sequence encoding said potato starch branching enzyme; wherein the second nucleic acid molecule does not encode antisense RNA to an exon of the genomic sequence.

13. The method according to claim 12 wherein the second nucleic acid molecule encodes an antisense RNA to intron 1 of potato starch branching enzyme.

14. A method of reducing starch branching enzymatic activity in a plant, or a cell, a tissue or an organ thereof, comprising expressing in the plant, or the cell, the tissue or organ thereof a nucleic acid molecule encoding antisense RNA to intron 1 of the potato starch branching enzyme, optionally under the control of the promoter of the potato starch branching enzyme.

15. The method according to claim 14 wherein levels of amylopectin are affected or the composition of starch is changed in the plant, or the cell, tissue or organ thereof.

16. The method according to claim 14 wherein the nucleic acid comprises the sequence shown as any one of SEQ. ID. No. 15 to SEQ. ID. No. 27.

17. The method according to claim 14 wherein the nucleic acid molecule is expressed by a promoter having a sequence comprising the sequence shown as SEQ ID NO. 14.

18. The method according to claim 16 wherein the nucleic acid molecule is expressed by a promoter having a sequence comprising the sequence shown as SEQ ID NO. 14.

19. A method of reducing starch branching enzymatic activity in a starch producing plant or a cell, a tissue, or an organ thereof, comprising expressing in the starch producing plant, the cell, the tissue or the organ thereof a nucleic acid molecule encoding antisense RNA to intron 1 of the potato starch branching enzyme, optionally under the control of the promoter of the potato starch branching enzyme.

20. The method according to claimed 19 wherein levels of amylopectin are affected or the composition of starch is changed in the starch producing plant, or the cell, tissue or organ thereof.

21. The method according to claim 19 wherein the nucleic acid comprises the sequence shown as any one of SEQ. ID. No. 15 to SEQ ID No. 27.

22. The method according to claim 19 wherein the nucleic acid molecule is expressed by a promoter having a sequence comprising the sequence shown as SEQ ID NO. 14.

23. The method according to claim 21 wherein the nucleic acid molecule is expressed by a promoter having a sequence comprising the sequence shown as SEQ ID NO. 14.

* * * * *

SEQUENCE LISTING

```
<160> NUMBER OF SEQ ID NOS: 33

<210> SEQ ID NO 1
<211> LENGTH: 1167
<212> TYPE: DNA
<213> ORGANISM: Solanum tuberosum

<400> SEQUENCE: 1 gtaatttta  ctaatttcat  gttaatttca  attattttta  gcctttgcat  ttcattttcc      60
aatatatctg  gatcatctcc  ttagtttttt  attttatttt  ttataatatc  aaatatggaa     120
gaaaaatgac  acttgtagag  ccatatgtaa  gtatcatgtg  acaaatttgc  aaggtggttg     180
agtgtataaa  attcaaaaat  tgagagatgg  agggggggtg  ggggbaraga  caatatttag     240
aaagagtgtt  ctaggaggtt  atggaggaca  cggatgaggg  gtagaaggtt  agttaggtat     300
ttgagtgttg  tctggcttat  cctttcatac  tagtagtcgt  ggaattattt  gggtagtttc     360
ttgttttgtt  atttgatctt  tgttattcta  ttttctgttt  cttgtacttc  gattattgta     420
ttatatatct  tgtcgtagtt  attgttcctc  ggtaagaatg  ctctagcatg  cttcctttag     480
```

-continued

```
tgttttatca tgccttcttt atattcgcgt tgctttgaaa tgcttttact ttagccgagg        540
gtctattaga aacaatctct ctatctcgta aggtagtgggt aaagtcctca ccacactcca       600
cttgtgggat tacattgtgt tgttgttgt aaatcaatta tgtatacata ataagtggat         660
tttttacaac acaaatacat ggtcaagggc aaagttctga acacataaag ggttcattat        720
atgtccaggg atatgataaa aattgtttct ttgtgaaagt tatataagat ttgttatggc        780
ttttgctgga aacataataa gttataatgc tgagatagct actgaagttt gttttttcta       840
gccttttaaa tgtaccaata atagattccg tatcgaacga gtatgttttg attacctggt       900
catgatgttt ctattttta cattttttg gtgttgaact gcaattgaaa atgttgtatc         960
ctatgagacg gatagttgag aatgtgttct ttgtatggac cttgagaagc tcaaacgcta      1020
ctccaataat ttctatgaat tcaaattcag tttatggcta ccagtcagtc cagaaattag      1080
gatatgctgc atatacttgt tcaattatac tgtaaaattt cttaagttct caagatatcc     1140
atgtaacctc gagaatttct ttgacag                                           1167

<210> SEQ ID NO 2
<211> LENGTH: 321
<212> TYPE: DNA
<213> ORGANISM: Solanum tuberosum

<400> SEQUENCE: 2
gtatgtttga taatttatat ggttgcatgg atagtatata aatagttgga aaacttctgg       60
actggtgctc atggcatatt tgatctgtgc accgtgtgga gatgtcaaac atgtgttact      120
tcgttccgcc aatttataat accttaactt gggaaagaca gctctttact cctgtgggca     180
tttgttattt gaattacaat ctttatgagc atggtgtttt cacattatca acttctttca     240
tgtggtatat aacagttttt agctccgtta ataccttct tctttttgat ataaactaac      300
tgtggtgcat tgcttgcbkk k                                                321

<210> SEQ ID NO 3
<211> LENGTH: 504
<212> TYPE: DNA
<213> ORGANISM: Solanum tuberosum

<400> SEQUENCE: 3
gtaacagcca aaagttgtgc tttaggcagt ttgaccttat tttggaagat gaattgttta       60
tacctacttt gactttgcta gagaattttg cataccgggg agtaagtagt ggctccattt      120
aggtggcacc tggccatttt tttgatcttt taaaaagctg tttgattggg tcttcaaaaa      180
agtagacaag gttttttggag aagtgacaca cccccggagt gtcagtggca aagcaaagat    240
tttcactaag gagattcaaa atataaaaaa agtatagaca taagaagct gagggggattc    300 aacatgtact atacaagcat caaatatagt cttaaagcaa ttttgtagaa ataaagaaag    360
tcttccttct gttgcttcac aatttccttc tattatcatg agttactctt tctgttcgaa    420
atagcttcct taatattaaa ttcatgatac ttttgttgag atttagcagt ttttttcttgt    480 gtaaactgct ctctttttt gcag                                             504

<210> SEQ ID NO 4
<211> LENGTH: 146
<212> TYPE: DNA
<213> ORGANISM: Solanum tuberosum

<400> SEQUENCE: 4
gtaggtcctc gtctactaca aaatagtagt ttccatcatc ataacagatt ttcctattaa       60
```

```
agcatgatgt tgcagcatca ttggctttct tacatgttct aattgctatt aaggttatgc    120
ttctaattaa ctcatccaca atgcag                                         146

<210> SEQ ID NO 5
<211> LENGTH: 218
<212> TYPE: DNA
<213> ORGANISM: Solanum tuberosum

<400> SEQUENCE: 5
gttttgttat tcataccttg aagctgaatt ttgaacacca tcatcacagg catttcgatt    60
catgttctta ctagtcttgt tatgtaagac attttgaaat gcaaaagtta aataattgt     120 gtctttacta atttggactt gatcccatac tctttccctt aacaaaatga gtcaattcta   180
taagtgcttg agaacttact acttcagcaa ttaaacag                           218

<210> SEQ ID NO 6
<211> LENGTH: 198
<212> TYPE: DNA
<213> ORGANISM: Solanum tuberosum

<400> SEQUENCE: 6 gtatttaaa tttatttcta caactaaata attctcagaa caattgttag atagaatcca     60
aatatatacg tcctgaaagt ataaaagtac ttattttcgc catgggcctt cagaatattg   120
gtagccgctg aatatcatga taagttattt atccagtgac attttatgt tcactcctat    180 tatgtctgct ggatacag                                                 198

<210> SEQ ID NO 7
<211> LENGTH: 208
<212> TYPE: DNA
<213> ORGANISM: Solanum tuberosum

<400> SEQUENCE: 7
gtttgtctgt ttctattgca ttttaaggtt catataggtt agccacggaa aatctcactc    60
tttgtgaggt aaccagggtt ctgatggatt attcaatttt ctcgtttatc atttgtttat   120
tcttttcatg cattgtgttt cttttcaat atccctctta tttggaggta attttctca    180 tctattcact tttagcttct aaccacag                                      208

<210> SEQ ID NO 8
<211> LENGTH: 293
<212> TYPE: DNA
<213> ORGANISM: Solanum tuberosum

<400> SEQUENCE: 8
gtatgtctta catctttaga tattttgtga taattacaat tagtttggct tacttgaaca    60
agattcattc ctcaaaatga cctgaactgt tgaacatcaa aggggttgaa acatagagga   120
aaacaacatg atgaatgttt ccattgtcta gggatttcta ttatgttgct gagaacaaat   180
gtcatcttaa aaaaaacatt gtttactttt ttgtagtata gaagattact gtatagagtt   240
tgcaagtgtg tctgttttgg agtaattgtg aaatgtttga tgaacttgta cag          293

<210> SEQ ID NO 9
<211> LENGTH: 376
<212> TYPE: DNA
<213> ORGANISM: Solanum tuberosum

<400> SEQUENCE: 9
```

```
gttcaagtat tttgaatcgc agcttgttaa ataatctagt aattttttaga ttgcttactt      60 ggaagtctac ttggttctgg ggatgatagc tcatttcatc ttgttctact tattttccaa     120
ccgaatttct gattttgtt tcgagatcca agtattgat tcatttacac ttattaccgc       180
ctcatttcta ccactaaggc cttgatgagc agcttaagtt gattctttga agctatagtt     240
tcaggctacc aatccacagc ctgctatatt tgttggatac ttaccttttc tttacaatga     300
agtgatacta attgaaatgg tctaaatctg atatctatat ttctccgtct ttcctccccc     360
tcatgatgaa atgcag                                                     376

<210> SEQ ID NO 10
<211> LENGTH: 172
<212> TYPE: DNA
<213> ORGANISM: Solanum tuberosum

<400> SEQUENCE: 10
gtaaaatcat ctaaagttga aagtgttggg tttatgaagt gctttaattc tatccaagga     60
caagtagaaa ccttttacc ttccatttct tgatgatgga tttcatatta tttaatccaa     120
tagctggtca aattcggtaa tagctgtact gattagttac ttcactttgc ag             172

<210> SEQ ID NO 11
<211> LENGTH: 145
<212> TYPE: DNA
<213> ORGANISM: Solanum tuberosum

<400> SEQUENCE: 11
gtatatatgt tttacttatc catgaaatta ttgctctgct tgttttaat gtactgaaca      60 agtttatgg agaagtaact gaaacaaatc attttcacat tgtctaattt aactctttt      120 tctgatcctc gcatgacgaa aacag                                           145

<210> SEQ ID NO 12
<211> LENGTH: 242
<212> TYPE: DNA
<213> ORGANISM: Solanum tuberosum

<400> SEQUENCE: 12
gtaaggattt gcttgaataa cttttgataa taagataaca gatgtagggt acagttctct     60
caccaaaaag aactgtaatt gtctcatcca tctttagttg tataagatat ccgactgtct    120
gagttcggaa gtgtttgagc ctcctgccct ccccctgcgt tgtttagcta attcaaaaag    180
gagaaaactg tttattgatg atctttgtct tcatgctgac atacaatctg ttctcatgac    240
ag                                                                    242

<210> SEQ ID NO 13
<211> LENGTH: 797
<212> TYPE: DNA
<213> ORGANISM: Solanum tuberosum

<400> SEQUENCE: 13
gtacagttct tgccgtgtga cctcccttt tattgtggtt ttgttcatag ttatttgaat      60
gcgatagaag ttaactattg attaccgcca caatcgccag ttaagtcctc tgaactacta    120
atttgaaagg taggaatagc cgtaataagg tctactttg gcatcttact gttacaaaac     180
aaaaggatgc caaaaaaatt cttctctatc ctctttttcc ctaaaccagt gcatgtagct    240
tgcacctgca taaacttagg taaatgatca aaaatgaagt tgatgggaac ttaaaaccgc    300
cctgaagtaa agctaggaat agtcatataa tgtccacctt tggtgtctgc gctaacatca    360
```

-continued

```
acaacaacat acctcgtgta gtcccacaaa gtggtttcag ggggagggta gagtgtatgc    420
aaaacttact cctatctcag aggtagagag gatttttca atagacccct ggctcaagaa    480
aaaaagtcca aaaagaagta acagaagtga aagcaacatg tgtagctaaa gcgacccaac    540
ttgtttggga ctgaagtagt tgttgttgtt gaaacagtgc atgtagatga acacatgtca    600
gaaaatggac aacacagtta ttttgtgcaa gtcaaaaaaa tgtactacta tttctttgtg    660
cagctttatg tatagaaaag ttaaataact aatgaatttt gctagcagaa aaatagcttg    720
gagagaaatt ttttatattg aactaagcta actatattca tctttctttt tgcttcttct    780
tctccttgtt tgtgaag                                                   797
```

```
<210> SEQ ID NO 14
<211> LENGTH: 2169
<212> TYPE: DNA
<213> ORGANISM: Solanum tuberosum

<400> SEQUENCE: 14
```

```
atcatggcca attactggtt caaatgcatt acttcctttc agattctttc gagttctcat     60
gaccggtcct actacagacg atactaaccc gtggaactgt tgcatctgct tcttagaact    120
ctatggctat tttcgttagc ttggcgtcgg tttgaacata gttttttgttt tcaaactctt    180 catttacagt caaaatgttg tatggttttt gttttcctca atgatgttta cagtgttgtg    240
ttgtcatctg tacttttgcc tattacttgt tttgagttac atgttaaaaa agtgtttatt    300
ttgccatatt ttgttctctt attattatta tcatacatac attattacaa ggaaaagaca    360
agtacacaga tcttaacgtt tatgttcaat caacttttgg aggcattgac aggtaccaca    420
aattttgagt ttatgattaa gttcaatctt agaatatgaa tttaacatct attatagatg    480
cataaaaata gctaatgata gaacattgac atttggcaga gcttagggta tggtatatcc    540
aacgttaatt tagtaatttt tgttacgtac gtatatgaaa tattgaatta atcacatgaa    600
cggtggatat tatattatga gttggcatca gcaaaatcat tggtgtagtt gactgtagtt    660
gcagatttaa taataaaatg gtaattaacg gtcgatatta aaataactct catttcaagt    720
gggattagaa ctagttatta aaaaaatgta tactttaagt gatttgatgg catataattt    780 aaagttttc atttcatgct aaaattgtta attattgtaa tgtagactgc gactggaatt    840
attatagtgt aaatttatgc attcagtgta aaattaaagt attgaacttg tctgttttag    900
aaaatacttt atacttaat ataggatttt gtcatgcgaa tttaaattaa tcgatattga    960
acacggaata ccaaaattaa aaaggataca catggccttc atatgaaccg tgaacctttg   1020
ataacgtgga agttcaaaga aggtaaagtt taagaataaa ctgacaaatt aatttctttt   1080
atttggccca ctactaaatt tgctttactt tctaacatgt caagttgtgc cctcttagtt   1140
gaatgatatt cattttcat cccataagtt caatttgatt gtcataccac ccatgatgtt   1200
ctgaaaaatg cttggccatt cacaaagttt atcttagttc ctatgaactt tataagaagc   1260
tttaatttga catgttattt atattagatg atataatcca tgacccaata gacaagtgta   1320
ttaatattgt aactttgtaa ttgagtgtgt ctacatctta ttcaatcatt taaggtcatt   1380
aaaataaatt attttttgac attctaaaac tttaagcaga ataaatagtt tatcaattat   1440
taaaaacaaa aaacgactta tttataaatc aacaaacaat tttagattgc tccaacatat   1500
ttttccaaat taaatgcaga aaatgcataa ttttatactt gatctttata gcttattttt   1560
tttagcctaa ccaacgaata tttgtaaact cacaacttga ttaaaaggga tttacaacaa   1620
```

-continued

```
gatatatata agtagtgaca aatcttgatt ttaaatattt taatttggag gtcaaaattt      1680
taccataatc atttgtattt ataattaaat tttaaatatc ttatttatac atatctagta      1740
aacttttaaa tatacgtata tacaaaatat aaaattattg gcgttcatat taggtcaata      1800
aatccttaac tatatctgcc ttaccactag gagaaagtaa aaaactcttt accaaaaata      1860
catgtattat gtatacaaaa agtcgattag attacctaaa tagaaattgt ataacgagta      1920
agtaagtaga aatataaaaa aactacaata ctaaaaaaaa tatgttttac ttcaatttcg      1980
aaactaatgg ggtctgagtg aaatattcag aaggggagg actaacaaaa gggtcataat        2040
gtttttttat aaaaagccac taaaatgagg aaatcaagaa tcagaacata caagaaggca      2100
gcagctgaag caaagtacca taatttaatc aatggaaatt aatttcaaag ttttatcaaa      2160
acccattcg                                                               2169
```

<210> SEQ ID NO 15
<211> LENGTH: 1167
<212> TYPE: DNA
<213> ORGANISM: Solanum tuberosum

<400> SEQUENCE: 15

```
ctgtcaaaga aattctcgag gttacatgga tatcttgaga acttaagaaa ttttacagta        60
taattgaaca agtatatgca gcatatccta atttctggac tgactggtag ccataaactg       120
aatttgaatt catagaaatt attggagtag cgtttgagct tctcaaggtc catacaaaga       180
acacattctc aactatccgt ctcataggat acaacatttt caattgcagt tcaacaccaa       240
aaaaatgtaa aaaatagaaa catcatgacc aggtaatcaa aacatactcg ttcgatacgg       300
aatctattat tggtacattt aaaaggctag aaaaaacaaa cttcagtagc tatctcagca       360
ttataactta ttatgtttcc agcaaaagcc ataacaaatc ttatataact ttcacaaaga       420
aacaattttt atcatatccc tggacatata atgaacccctt tatgtgttca gaactttgcc       480
cttgaccatg tatttgtgtt gtaaaaaatc cacttattat gtatacataa ttgatttaca       540
acaacaaaca caatgtaatc ccacaagtgg agtgtggtga ggactttacc cctaccttac       600
gagatagaga gattgtttct aatagacccct cggctaaagt aaaagcattt caaagcaacg       660
cgaatataaa gaaggcatga taaaacacta aggaagcat gctagagcat tcttaccgag        720
gaacaataac tacgacaaga tatataatac aataatcgaa gtacaagaaa cagaaaatag       780
aataacaaag atcaaataac aaaacaagaa actacccaaa taattccacg actactagta       840
tgaaaggata agccagacaa cactcaaata cctaactaac cttctacccc tcatccgtgt       900
cctccataac ctcctagaac actctttcta aatattgtct ytvcccccac cccccctcca       960
tctctcaatt tttgaatttt atacactcaa ccaccttgca aatttgtcac atgatactta      1020
catatggctc tacaagtgtc attttcttc catatttgat attataaaaa ataaaataaa       1080
aaactaagga gatgatccag atatattgga aaatgaaatg caaaggctaa aaataattga      1140
aattaacatg aaattagtaa aaattac                                           1167
```

<210> SEQ ID NO 16
<211> LENGTH: 321
<212> TYPE: DNA
<213> ORGANISM: Solanum tuberosum

<400> SEQUENCE: 16

```
mmmvgcaagc aatgcaccac agttagttta tatcaaaaag aagaaaggta ttaacggagc        60
taaaaactgt tatataccac atgaaagaag ttgataatgt gaaaacacca tgctcataaa       120
```

```
gattgtaatt caaataacaa atgcccacag gagtaaagag ctgtctttcc caagttaagg    180
tattataaat tggcggaacg aagtaacaca tgtttgacat ctccacacgg tgcacagatc    240
aaatatgcca tgagcaccag tccagaagtt ttccaactat ttatatacta tccatgcaac    300
catataaatt atcaaacata c                                              321
```

<210> SEQ ID NO 17
<211> LENGTH: 504
<212> TYPE: DNA
<213> ORGANISM: Solanum tuberosum

<400> SEQUENCE: 17

```
ctgcaaaaaa agagagcagt ttacacaaga aaaactgct aaatctcaac aaaagtatca     60
tgaatttaat attaaggaag ctatttcgaa cagaaagagt aactcatgat aatagaagga    120
aattgtgaag caacagaagg aagactttct ttatttctac aaaattgctt taagactata    180
tttgatgctt gtatagtaca tgttgaatcc cctcagcttc tttatgtcta actttttttt    240
atattttgaa tctccttagt gaaaatcttt gctttgccac tgacactccg ggggtgtgtc    300
acttctccaa aaaccttgtc tacttttttg aagacccaat caaacagctt tttaaaagat    360 caaaaaatg gccaggtgcc acctaaatgg agccactact tactccccgg tatgcaaaat    420
tctctagcaa agtcaaagta ggtataaaca attcatcttc caaaataagg tcaaactgcc    480
taaagcacaa cttttggctg ttac                                           504
```

<210> SEQ ID NO 18
<211> LENGTH: 146
<212> TYPE: DNA
<213> ORGANISM: Solanum tuberosum

<400> SEQUENCE: 18

```
ctgcattgtg gatgagttaa ttagaagcat aaccttaata gcaattagaa catgtaagaa     60
agccaatgat gctgcaacat catgctttaa taggaaaatc tgttatgatg atggaaacta    120
ctattttgta gtagacgagg acctac                                         146
```

<210> SEQ ID NO 19
<211> LENGTH: 218
<212> TYPE: DNA
<213> ORGANISM: Solanum tuberosum

<400> SEQUENCE: 19

```
ctgtttaatt gctgaagtag taagttctca agcacttata gaattgactc attttgttaa     60
gggaaagagt atgggatcaa gtccaaatta gtaaagacac aattattta acttttgcat    120 ttcaaaatgt cttacataac aagactagta agaacatgaa tcgaaatgcc tgtgatgatg    180
gtgttcaaaa ttcagcttca aggtatgaat aacaaaac                            218
```

<210> SEQ ID NO 20
<211> LENGTH: 198
<212> TYPE: DNA
<213> ORGANISM: Solanum tuberosum

<400> SEQUENCE: 20

```
ctgtatccag cagacataat aggagtgaac ataaaaatgt cactggataa ataacttatc     60
atgatattca gcggctacca atattctgaa ggccctggc gaaataagt actttatac     120 tttcaggacg tatatatttg gattctatct aacaattgtt ctgagaatta tttagttgta    180
```

-continued

| gaaataaatt taaaatac | 198 |

<210> SEQ ID NO 21
<211> LENGTH: 208
<212> TYPE: DNA
<213> ORGANISM: Solanum tuberosum

<400> SEQUENCE: 21

| ctgtggttag aagctaaaag tgaatagatg agaaaaatta cctccaaata agagggatat | 60 |
| tgaaaaagaa acacaatgca tgaaagaat aaacaaatga taaacgagaa aattgaataa | 120 |
| tccatcagaa ccctggttac ctcacaaaga gtgagatttt ccgtggctaa cctatatgaa | 180 |
| ccttaaaatg caatagaaac agacaaac | 208 |

<210> SEQ ID NO 22
<211> LENGTH: 293
<212> TYPE: DNA
<213> ORGANISM: Solanum tuberosum

<400> SEQUENCE: 22

| ctgtacaagt tcatcaaaca tttcacaatt actccaaaac agacacactt gcaaactcta | 60 |
| tacagtaatc ttctatacta caaaaaagta aacaatgttt tttttaagat gacatttgtt | 120 |
| ctcagcaaca taatagaaat ccctagacaa tggaaacatt catcatgttg ttttcctcta | 180 |
| tgtttcaacc cctttgatgt tcaacagttc aggtcatttt gaggaatgaa tcttgttcaa | 240 |
| gtaagccaaa ctaattgtaa ttatcacaaa atatctaaag atgtaagaca tac | 293 |

<210> SEQ ID NO 23
<211> LENGTH: 376
<212> TYPE: DNA
<213> ORGANISM: Solanum tuberosum

<400> SEQUENCE: 23

| ctgcatttca tcatgagggg gaggaaagac ggagaaatat agatatcaga tttagaccat | 60 |
| ttcaattagt atcacttcat tgtaaagaaa aggtaagtat ccaacaaata tagcaggctg | 120 |
| tggattggta gcctgaaact atagcttcaa agaatcaact taagctgctc atcaaggcct | 180 |
| tagtggtaga atgaggcgg taataagtgt aaatgaatct aatacttgga tctcgaaaca | 240 |
| aaaatcagaa attcggttgg aaaataagta gaacaagatg aaatgagcta tcatccccag | 300 |
| aaccaagtag acttccaagt aagcaatcta aaaattacta gattatttaa caagctgcga | 360 |
| ttcaaaatac ttgaac | 376 |

<210> SEQ ID NO 24
<211> LENGTH: 172
<212> TYPE: DNA
<213> ORGANISM: Solanum tuberosum

<400> SEQUENCE: 24

| ctgcaaagtg aagtaactaa tcagtacagc tattaccgaa tttgaccagc tattggatta | 60 |
| aataatatga aatccatcat caagaaatgg aaggtaaaaa ggtttctact tgtccttgga | 120 |
| tagaattaaa gcacttcata aacccaacac tttcaacttt agatgatttt ac | 172 |

<210> SEQ ID NO 25
<211> LENGTH: 145
<212> TYPE: DNA
<213> ORGANISM: Solanum tuberosum

<400> SEQUENCE: 25

```
ctgttttcgt catgcgagga tcagaaaaaa gagttaaatt agacaatgtg aaaatgattt    60
gtttcagtta cttctccata aaacttgttc agtacattaa aaacaagcag agcaataatt   120
tcatggataa gtaaaacata tatac                                        145

<210> SEQ ID NO 26
<211> LENGTH: 242
<212> TYPE: DNA
<213> ORGANISM: Solanum tuberosum

<400> SEQUENCE: 26
ctgtcatgag aacagattgt atgtcagcat gaagacaaag atcatcaata aacagttttc    60
tcctttttga attagctaaa caacgcaggg ggagggcagg aggctcaaac acttccgaac   120
tcagacagtc ggatatctta tacaactaaa gatggatgag acaattacag ttcttttttgg  180 tgagagaact gtaccctaca tctgttatct tattatcaaa agttattcaa gcaaatcctt   240
ac                                                                 242

<210> SEQ ID NO 27
<211> LENGTH: 797
<212> TYPE: DNA
<213> ORGANISM: Solanum tuberosum

<400> SEQUENCE: 27
cttcacaaac aaggagaaga agaagcaaaa agaaagatga atatagttag cttagttcaa    60
tataaaaaat ttctctccaa gctattttttc tgctagcaaa attcattagt tatttaactt   120
ttctatacat aaagctgcac aaagaaatag tagtacattt ttttgacttg cacaaaataa   180
ctgtgttgtc cattttctga catgtgttca tctacatgca ctgtttcaac aacaacaact   240
acttcagtcc caaacaagtt gggtcgcttt agctacacat gttgctttca cttctgttac   300 ttcttttttgg acttttttttc ttgagccaag ggtctattga aaaaatcctc tctacctctg   360
agataggagt aagttttgca tacactctac cctcccctg aaaccactttt gtgggactac   420 acgaggtatg ttgttgttga tgttagcgca gacaccaaag gtggacatta tatgactatt   480
cctagcttta cttcagggcg gttttaagtt cccatcaact tcattttga tcatttacct   540 aagtttatgc aggtgcaagc tacatgcact ggtttaggga aaaagaggat agagaagaat   600
ttttttggca tcctttttgtt ttgtaacagt aagatgccaa aagtagacct tattacggct   660
attcctacct ttcaaattag tagttcagag gacttaactg gcgattgtgg cggtaatcaa   720
tagttaactt ctatcgcatt caaataacta tgaacaaaac cacaataaaa agggaggtca   780
cacggcaaga actgtac                                                 797

<210> SEQ ID NO 28
<211> LENGTH: 2169
<212> TYPE: DNA
<213> ORGANISM: Solanum tuberosum

<400> SEQUENCE: 28
cgaatgggtt ttgataaaac tttgaaatta atttccattg attaaattat ggtactttgc    60
ttcagctgct gccttcttgt atgttctgat tcttgatttc ctcattttag tggcttttta   120
taaaaaaaca ttatgacct tttgttagtc ctccccttc tgaatatttc actcagaccc   180
cattagtttc gaaattgaag taaaacatat ttttttttagt attgtagttt ttttatattt   240
ctacttactt actcgttata caatttctat ttaggtaatc taatcgactt tttgtataca   300
```

```
taatacatgt attttggta aagagtttt tactttctcc tagtggtaag gcagatatag       360
ttaaggattt attgacctaa tatgaacgcc aataattta tattttgtat atacgtatat       420
ttaaaagttt actagatatg tataaataag atatttaaaa tttaattata aatacaaatg       480
attatggtaa aattttgacc tccaaattaa aatatttaaa atcaagattt gtcactactt       540
atatatatct tgttgtaaat ccctttaat caagttgtga gttacaaat attcgttggt       600 taggctaaaa aaataagct ataaagatca agtataaaat tatgcatttt ctgcatttaa       660
tttgaaaaaa tatgttggag caatctaaaa ttgtttgttg atttataaat aagtcgtttt       720 ttgttttaa taattgataa actatttatt ctgcttaaag ttttagaatg tcaaaaaata       780
atttatttta atgaccttaa atgattgaat aagatgtaga cacactcaat tacaaagtta       840
caatattaat acacttgtct attgggtcat ggattatatc atctaatata aataacatgt       900
caaattaaag cttcttataa agttcatagg aactaagata aactttgtga atggccaagc       960 attttttcaga acatcatggg tggtatgaca atcaaattga acttatggga tgaaaaatga      1020
atatcattca actaagaggg cacaacttga catgttagaa agtaaagcaa atttagtagt      1080
gggccaaata aaagaaatta atttgtcagt ttattcttaa actttacctt ctttgaactt      1140
ccacgttatc aaaggttcac ggttcatatg aaggccatgt gtatccttt taattttggt      1200 attccgtgtt caatatcgat taatttaaat tcgcatgaca aaatcctata ttaaagtata      1260
aagtattttc taaaacagac aagttcaata cttaattttt acactgaatg cataaattta      1320
cactataata attccagtcg cagtctcat tacaataatt aacaatttta gcatgaaatg      1380
aaaaacttta aattatatgc catcaaatca cttaaagtat acatttttt aataactagt      1440 tctaatccca cttgaaatga gagttatttt aatatcgacc gttaattacc attttattat      1500
taaatctgca actacagtca actacaccaa tgattttgct gatgccaact cataatataa      1560
tatccaccgt tcatgtgatt aattcaatat ttcatatacg tacgtaacaa aaattactaa      1620
attaacgttg gatataccat accctaagct ctgccaaatg tcaatgttct atcattagct      1680
atttttatgc atctataata gatgttaaat tcatattcta agattgaact taatcataaa      1740
ctcaaaattt gtggtacctg tcaatgcctc caaagttga ttgaacataa acgttaagat      1800
ctgtgtactt gtcttttcct tgtaataatg tatgtatgat aataataata agagaacaaa      1860
atatggcaaa ataaacactt ttttaacatg taactcaaaa caagtaatag gcaaaagtac      1920
agatgacaac acaacactgt aaacatcatt gaggaaaaca aaaaccatac aacattttga      1980
ctgtaaatga agagtttgaa aacaaaaact atgttcaaac cgacgccaag ctaacgaaaa      2040
tagccataga gttctaagaa gcagatgcaa cagttccacg ggttagtatc gtctgtagta      2100
ggaccggtca tgagaactcg aaagaatctg aaaggaagta atgcatttga accagtaatt      2160
ggccatgat                                                              2169
```

<210> SEQ ID NO 29
<211> LENGTH: 11478
<212> TYPE: DNA
<213> ORGANISM: Solanum tuberosum

<400> SEQUENCE: 29

```
atcatggcca attactggtt caaatgcatt acttcctttc agattctttc gagttctcat        60
gaccggtcct actacagacg atactaaccc gtggaactgt tgcatctgct tcttagaact       120
ctatggctat tttcgttagc ttggcgtcgg tttgaacata gttttgttt tcaaactctt       180 catttacagt caaaatgttg tatggttttt gttttcctca atgatgttta cagtgttgtg       240
```

```
ttgtcatctg tacttttgcc tattacttgt tttgagttac atgttaaaaa agtgtttatt    300
ttgccatatt ttgttctctt attattatta tcatacatac attattacaa ggaaaagaca    360
agtacacaga tcttaacgtt tatgttcaat caacttttgg aggcattgac aggtaccaca    420
aattttgagt ttatgattaa gttcaatctt agaatatgaa tttaacatct attatagatg    480
cataaaaata gctaatgata gaacattgac atttggcaga gcttagggta tggtatatcc    540
aacgttaatt tagtaatttt tgttacgtac gtatatgaaa tattgaatta atcacatgaa    600
cggtggatat tatattatga gttggcatca gcaaaatcat tggtgtagtt gactgtagtt    660
gcagatttaa taataaaatg gtaattaacg gtcgatatta aaataactct catttcaagt    720
gggattagaa ctagttatta aaaaaatgta tactttaagt gatttgatgg catataattt    780 aaagttttc atttcatgct aaaattgtta attattgtaa tgtagactgc gactggaatt    840
attatagtgt aaatttatgc attcagtgta aaattaaagt attgaacttg tctgttttag    900
aaaatacttt atactttaat ataggatttt gtcatgcgaa tttaaattaa tcgatattga    960
acacggaata ccaaaattaa aaaggataca catggccttc atatgaaccg tgaacctttg    1020
ataacgtgga agttcaaaga aggtaaagtt taagaataaa ctgacaaatt aatttctttt    1080
atttggccca ctactaaatt tgctttactt tctaacatgt caagttgtgc cctcttagtt    1140
gaatgatatt cattttcat cccataagtt caatttgatt gtcataccac ccatgatgtt    1200
ctgaaaaatg cttggccatt cacaaagttt atcttagttc ctatgaactt tataagaagc    1260
tttaatttga catgttattt atattagatg atataatcca tgacccaata gacaagtgta    1320
ttaatattgt aactttgtaa ttgagtgtgt ctacatctta ttcaatcatt taaggtcatt    1380
aaaataaatt attttttgac attctaaaac tttaagcaga ataaatagtt tatcaattat    1440
taaaaacaaa aaacgactta tttataaatc aacaaacaat tttagattgc tccaacatat    1500
ttttccaaat taaatgcaga aaatgcataa ttttatactt gatctttata gcttattttt    1560
tttagcctaa ccaacgaata tttgtaaact cacaacttga ttaaaaggga tttacaacaa    1620
gatatatata agtagtgaca aatcttgatt ttaaatattt taatttggag gtcaaaattt    1680
taccataatc atttgtattt ataattaaat tttaaatatc ttatttatac atatctagta    1740
aacttttaaa tatacgtata tacaaaatat aaaattattg gcgttcatat taggtcaata    1800
aatccttaac tatatctgcc ttaccactag gagaaagtaa aaaactcttt accaaaaata    1860
catgtattat gtatacaaaa agtcgattag attacctaaa tagaaattgt ataacgagta    1920
agtaagtaga aatataaaaa aactacaata ctaaaaaaaa tatgttttac ttcaatttcg    1980
aaactaatgg ggtctgagtg aaatattcag aaagggggagg actaacaaaa gggtcataat    2040 gttttttat aaaaagccac taaaatgagg aaatcaagaa tcagaacata caagaaggca    2100
gcagctgaag caaagtacca taatttaatc aatggaaatt aatttcaaag ttttatcaaa    2160
acccattcga ggatcttttc catctttctc acctaaagtt tcttcagggg taattttttac    2220 taatttcatg ttaatttcaa ttattttag cctttgcatt tcattttcca atatatctgg    2280
atcatctcct tagttttttta ttttattttt tataatatca aatatggaag aaaaatgaca    2340
cttgtagagc catatgtaag tatcatgtga caaatttgca aggtggttga gtgtataaaa    2400
ttcaaaaatt gagagatgga ggggggtgg gggbaragac aatatttaga aagagtgttc    2460
taggaggtta tggaggacac ggatgagggg tagaaggtta gttaggtatt tgagtgttgt    2520
ctggcttatc ctttcatact agtagtcgtg gaattatttg ggtagtttct tgttttgtta    2580
```

```
tttgatcttt gttattctat tttctgtttc ttgtacttcg attattgtat tatatatctt    2640
gtcgtagtta ttgttcctcg gtaagaatgc tctagcatgc ttcctttagt gttttatcat    2700
gccttcttta tattcgcgtt gctttgaaat gcttttactt tagccgaggg tctattagaa    2760
acaatctctc tatctcgtaa ggtaggggta aagtcctcac cacactccac ttgtgggatt    2820
acattgtgtt tgttgttgta aatcaattat gtatacataa taagtggatt ttttacaaca    2880
caaatacatg gtcaagggca aagttctgaa cacataaagg gttcattata tgtccaggga    2940
tatgataaaa attgtttctt tgtgaaagtt atataagatt tgttatggct tttgctggaa    3000
acataataag ttataatgct gagatagcta ctgaagtttg ttttttctag cctttttaaat   3060
gtaccaataa tagattccgt atcgaacgag tatgttttga ttacctggtc atgatgtttc    3120
tattttttac attttttttgg tgttgaactg caattgaaaa tgttgtatcc tatgagacgg   3180
atagttgaga atgtgttctt tgtatggacc ttgagaagct caaacgctac tccaataatt    3240
tctatgaatt caaattcagt ttatggctac cagtcagtcc agaaattagg atatgctgca    3300
tatacttgtt caattatact gtaaaatttc ttaagttctc aagatatcca tgtaacctcg    3360
agaatttctt tgacaggctt ctagaaataa gatatgtttt ccttctcaac atagtactgg    3420
actgaagttt ggatctcagg aacggtcttg ggatatttct tccacccaa aatcaagagt     3480
tagaaaagat gaaagggtat gtttgataat ttatatggtt gcatggatag tatataaata    3540
gttgaaaaac ttctggactg gtgctcatgg catatttgat ctgtgcaccg tgtggagatg    3600
tcaaacatgt gttacttcgt tccgccaatt tataatacct taacttggga aagacagctc    3660
tttactcctg tgggcatttg ttatttgaat tacaatcttt atgagcatgg tgttttcaca    3720
ttatcaactt ctttcatgtg gtatataaca gttttttagct ccgttaatac ctttcttctt   3780
tttgatataa actaactgtg gtgcattgct tgcbkkkatg aagcacagtt cagctatttc    3840
cgctgttttg accgatgacg acaattcgac aatggcaccc ctagaggaag atgtcaagac    3900
tgaaaatatt ggcctcctaa atttggatcc aactttggaa ccttatctag atcacttcag    3960
acacagaatg aagagatatg tggatcagaa aatgctcatt gaaaaatatg agggacccct    4020
tgaggaattt gctcaaggta acagccaaaa gttgtgcttt aggcagtttg accttatttt    4080
ggaagatgaa ttgtttatac ctactttgac tttgctagag aattttgcat accgggaggt    4140
aagtagtggc tccatttagg tggcacctgg ccattttttt gatctttaa aaagctgttt     4200
gattgggtct tcaaaaaagt agacaaggtt tttggagaag tgacacaccc ccggagtgtc    4260
agtggcaaag caaagatttt cactaaggag attcaaaata taaaaaagt atagacataa     4320
agaagctgag gggattcaac atgtactata caagcatcaa atatagtctt aaagcaattt    4380
tgtagaaata aagaaagtct tccttctgtt gcttcacaat ttccttctat tatcatgagt    4440
tactctttct gttcgaaata gcttccttaa tattaaattc atgatacttt tgttgagatt    4500
tagcagtttt ttcttgtgta aactgctctc ttttttttgca ggttatttaa aatttggatt   4560
caacagggaa gatggttgca tagtctatcg tgaatgggct cctgctgctc agtaggtcct    4620
cgtctactac aaaatagtag tttccatcat cataacagat tttcctatta aagcatgatg    4680
ttgcagcatc attggctttc ttacatgttc taattgctat taaggttatg cttctaatta    4740
actcatccac aatgcaggga agcagaagtt attggcgatt tcaatggatg gaacggttct    4800
aaccacatga tggagaagga ccagtttggt gtttggagta ttagaattcc tgatgttgac    4860
agtaagccag tcattccaca caactccaga gttaagtttc gtttcaaaca tggtaatgga    4920
gtgtgggtag atcgtatccc tgcttggata aagtatgcca ctgcagacgc cacaaagttt    4980
```

```
gcagcaccat atgatggtgt ctactgggac ccaccacctt cagaaaggtt ttgttattca    5040
taccttgaag ctgaattttg aacaccatca tcacaggcat ttcgattcat gttcttacta    5100
gtcttgttat gtaagacatt ttgaaatgca aaagttaaaa taattgtgtc tttactaatt    5160
tggacttgat cccatactct ttcccttaac aaaatgagtc aattctataa gtgcttgaga    5220
acttactact tcagcaatta aacaggtacc acttcaaata ccctcgccct cccaaacccc    5280
gagccccacg aatctatgaa gcacatgtcg gcatgagcag ctctgagcca cgtgtaaatt    5340
cgtatcgtga gtttgcagat gatgttttac ctcggattaa ggcaaataac tataatactg    5400
tccagttgat ggccataatg gaacattctt actatggatc atttggatat catgttacaa    5460
acttttttgc tgtgagcagt agatatggaa acccggagga cctaaagtat ctgatagata    5520
aagcacatag cttgggttta caggttctgg tggatgtagt tcacagtcat gcaagcaata    5580
atgtcactga tggcctcaat ggctttgata ttggccaagg ttctcaagaa tcctactttc    5640
atgctggaga gcgagggtac cataagttgt gggatagcag gctgttcaac tatgccaatt    5700
gggaggttct tcgtttcctt ctttccaact tgaggtggtg gctagaagag tataactttg    5760
acggatttcg atttgatgga ataacttcta tgctgtatgt tcatcatgga atcaatatgg    5820
gatttacagg aaactataat gagtatttca gcgaggctac agatgttgat gctgtggtct    5880
atttaatgtt ggccaataat ctgattcaca agattttccc agatgcaact gttattgccg    5940
aagatgtttc tggtatgccg ggccttggcc ggcctgtttc tgaggagga attggttttg    6000 tttaccgcct ggcaatggca atcccagata agtggataga ttatttaaag aataagaatg    6060
atgaagattg gtccatgaag gaagtaacat cgagtttgac aaataggaga tatacagaga    6120
agtgtatagc atatgcggag acccatgatc aggtatttta aatttatttc tacaactaaa    6180
taattctcag aacaattgtt agatagaatc caaatatata cgtcctgaaa gtataaaagt    6240
acttattttc gccatgggcc ttcagaatat tggtagccgc tgaatatcat gataagttat    6300
ttatccagtg acattttat gttcactcct attatgtctg ctggatacag tctattgttg    6360
gtgacaagac cattgcattt ctcctaatgg acaaagagat gtattctggc atgtcttgct    6420
tgacagatgc ttctcctgtt gttgatcgag gaattgcgct tcacaaggtt tgtctgtttc    6480
tattgcattt taaggttcat ataggttagc cacggaaaat ctcactcttt gtgaggtaac    6540
cagggttctg atggattatt caattttctc gtttatcatt tgtttattct tttcatgcat    6600
tgtgtttctt tttcaatatc cctcttattt ggaggtaatt tttctcatct attcacttt     6660 agcttctaac cacagatgat ccatttttc acaatggcct tgggaggaga ggggtacctc    6720
aatttcatgg gtaacgaggt atgtcttaca tctttagata ttttgtgata attacaatta    6780
gtttggctta cttgaacaag attcattcct caaaatgacc tgaactgttg aacatcaaag    6840
gggttgaaac atagaggaaa acaacatgat gaatgtttcc attgtctagg gatttctatt    6900
atgttgctga gaacaaatgt catcttaaaa aaaacattgt ttactttttt gtagtataga    6960
agattactgt atagagtttg caagtgtgtc tgttttggag taattgtgaa atgtttgatg    7020
aacttgtaca gtttggccat cctgagtgga ttgacttccc tagagagggc ataattgga     7080 gttatgacaa atgtagacgc cagtggaacc tcgcggatag cgaacacttg agatacaagg    7140
ttcaagtatt ttgaatcgca gcttgttaaa taatctagta attttttagat tgcttacttg    7200 gaagtctact tggttctggg gatgatagct catttcatct tgttctactt attttccaac    7260
cgaatttctg atttttgttt cgagatccaa gtattagatt catttacact tattaccgcc    7320
```

-continued

```
tcatttctac cactaaggcc ttgatgagca gcttaagttg attctttgaa gctatagttt    7380
caggctacca atccacagcc tgctatattt gttggatact tacctttct ttacaatgaa     7440 gtgatactaa ttgaaatggt ctaaatctga tatctatatt tctccgtctt tcctccccct    7500
catgatgaaa tgcagtttat gaatgcattt gatagagcta tgaattcgct cgatgaaaag    7560
ttctcattcc tcgcatcagg aaaacagata gtaagcagca tggatgatga taataaggta    7620
aaatcatcta agttgaaag tgttgggttt atgaagtgct ttaattctat ccaaggacaa     7680
gtagaaacct ttttaccttc catttcttga tgatggattt catattattt aatccaatag    7740
ctggtcaaat tcggtaatag ctgtactgat tagttacttc actttgcagg ttgttgtgtt    7800
tgaacgtggt gacctggtat ttgtattcaa cttccaccca aagaacacat acgaagggta    7860
tatatgtttt acttatccat gaaattattg ctctgcttgt ttttaatgta ctgaacaagt    7920
tttatggaga agtaactgaa acaaatcatt ttcacattgt ctaatttaac tcttttttct    7980
gatcctcgca tgacgaaaac aggtataaag ttggatgtga cttgccaggg aagtacagag    8040
ttgcactgga cagtgatgct tgggaatttg gtggccatgg aagagtaagg atttgcttga    8100
ataacttttg ataataagat aacagatgta gggtacagtt ctctcaccaa aaagaactgt    8160
aattgtctca tccatcttta gttgtataag atatccgact gtctgagttc ggaagtgttt    8220
gagcctcctg ccctccccct gcgttgttta gctaattcaa aaaggagaaa actgtttatt    8280
gatgatcttt gtcttcatgc tgacatacaa tctgttctca tgacagactg gtcatgatgt    8340
tgaccatttc acatcaccag aaggaatacc tggagttcca gaaacaaatt tcaatggtcg    8400
tccaaattcc ttcaaagtgc tgtctcctgc gcgaacatgt gtggtacagt tcttgccgtg    8460
tgacctccct ttttattgtg gttttgttca tagttatttg aatgcgatag aagttaacta    8520
ttgattaccg ccacaatcgc cagttaagtc ctctgaacta ctaatttgaa aggtaggaat    8580
agccgtaata aggtctactt ttggcatctt actgttacaa acaaaagga tgccaaaaaa     8640 attcttctct atcctctttt tccctaaacc agtgcatgta gcttgcacct gcataaactt    8700
aggtaaatga tcaaaatga agttgatggg aacttaaaac cgccctgaag taaagctagg    8760
aatagtcata taatgtccac ctttggtgtc tgcgctaaca tcaacaacaa catacctcgt    8820
gtagtcccac aaagtggttt caggggagg gtagagtgta tgcaaaactt actcctatct    8880
cagaggtaga gaggattttt tcaatagacc cttggctcaa gaaaaaaagt ccaaaaagaa    8940
gtaacagaag tgaaagcaac atgtgtagct aaagcgaccc aacttgtttg ggactgaagt    9000
agttgttgtt gttgaaacag tgcatgtaga tgaacacatg tcagaaaatg gacaacacag    9060 ttatttgtg caagtcaaaa aaatgtacta ctatttcttt gtgcagcttt atgtatagaa     9120
aagttaaata actaatgaat tttgctagca gaaaaatagc ttggagagaa atttttata    9180 ttgaactaag ctaactatat tcatcttttct ttttgcttct tcttctccttt gtttgtgaag   9240 gcttattaca gagttgatga acgcatgtca gaaactgaag attaccagac agacatttgt    9300
agtgagctac taccaacagc caatatcgag gagagtgacg agaaacttaa agattcgtta    9360
tctacaaata tcagtaacat tgacgaacgc atgtcagaaa ctgaagttta ccagacagac    9420
atttctagtg agctactacc aacagccaat attgaggaga gtgacgagaa acttaaagat    9480
tcgttatcta caaatatcag taacattgat cagactgttg tagtttctgt tgaggagaga    9540
gacaaggaac ttaaagattc accgtctgta agcatcatta gtgatgttgt tccagctgaa    9600
tgggatgatt cagatgcaaa cgtctggggt gaggactagt cagatgattg atcgacccttt   9660 ctaccgattg gtgatcgcta tccttgctct ctgagaaata ggtgaggcga aacaaaaat     9720
```

```
aatttgcatg ataaaaagtc tgattttatg atcgctatcc tcgctctctg agaaagaagc    9780
gaaacaaagg cgactcctgg actcgaatct ataagataac aaaggcgact cctgggactc    9840
gaatctataa gataacaaag gcaattccaa gacttgaatc tataaaaaat ttagttaaga    9900
atgattaacg tccgatccta attcgaatcg aggcatctta ccactccatt gataattata    9960
taagtcaata agtcatataa wagtattaaa aactaaattg acttgatcgg tctatcaaaa   10020
atmagatmaa attgtgttca tatgtaacat ttttgttgtc acaattagct taattacatc   10080
tttcatgtgc aataacaaag aaatgatagg aatttagaga ttccaatttt tttgttgcca   10140
caattaactt aattacatct ttcatttgca ataacaaaga aatgatagga atttagagat   10200
ccagtgtcaa tacacaacct aggccaacat cgaaagcata actgtaaact catgcatgaa   10260
gaaatcagtc gtaaaaatga ataaatgcga cataaaaaca aattgcatgt atcattaatg   10320
tgacttaact acaagtaaaa ataaatttaa caaatgtaac ttaactacaa gtaaaaataa   10380
attgcttcta tcattaacaa acaaacagaa ttaaaaagaa aaaaacatac taaatcttac   10440
cgtcattcga taaaaaaaaa taccaaattc ataatgcaag gaaaacgaaa cgcgtcctga   10500
tcgggtatca acgatgaaat ggaccagttg gatcgactgc ctgcacaacg ttaggtatgc   10560
caaaaaaaag aacacgatcc tttgcacccg ttcgatgatt atcagtatgt tcacaaaaaa   10620
aacttaagtt catcccagtg tacaacagcc ccaacatctg ccccaagtaa caaaaaacaa   10680
ccaatttatc ttattcttat ctgccacaaa ataatcggtt tcacactatt ctcttgttat   10740
acaaaattga caagtaggaa ggagaggagt catccaaata aacggtgcac gttctttgag   10800
aaaagtctta tttttcgtaa gatccaattt caacaaactt ttcttcaagt caaaattcct   10860
gatagtgtat ctcctctcga cgacctcttg cattgaacga tctccgctta tcatgaaaag   10920
ttgcttggat aacaagtatt gcaagggggg gacagtagct attaagttag tcggcccaag   10980
gaaatggagg agtgatagtc tcgaatatta ttcacctctt tagcattacc cggtctggct   11040
ttaaggagtt acgtctttta cgctcgccaa tttctttttt tagaatggtt ggtgtcaaaa   11100
tcgcgagttg tggaaggttc aagttactcg attcgtgatt ttcaagtatg agtggtgaga   11160
gagattcgat attttcacga ggtgtattcg aggtctagta gaacgaaggg tgtcactaat   11220
gaaagtttca agagttcatc atcatcttct tctagtagat tttcgctttc aaatgagtat   11280
gaaaattctt cctcttttct attgattttc ttcattgttt tcttcattgt tgtggttgtt   11340
attgaaaaga aagaaaattt ataacagaaa aagatgtcaa aaaaaaggta aaatgaaaga   11400
gtatcatata cttaaagagt tgcgtagaga taagtcaaaa gaaacagaat tatagtaatt   11460
tcagctaagt tagaattc                                                 11478

<210> SEQ ID NO 30
<211> LENGTH: 26
<212> TYPE: DNA
<213> ORGANISM: Solanum tuberosum

<400> SEQUENCE: 30
ggaattccag tcgcagtcta cattac                                              26

<210> SEQ ID NO 31
<211> LENGTH: 28
<212> TYPE: DNA
<213> ORGANISM: Solanum tuberosum

<400> SEQUENCE: 31
```

-continued

```
cgggatccag aggcattaag atttctgg                                          28

<210> SEQ ID NO 32
<211> LENGTH: 32
<212> TYPE: DNA
<213> ORGANISM: Solanum tuberosum

<400> SEQUENCE: 32
cgggatccaa agaaattctc gaggttacat gg                                     32

<210> SEQ ID NO 33
<211> LENGTH: 32
<212> TYPE: DNA
<213> ORGANISM: Solanum tuberosum

<400> SEQUENCE: 33
cgggatccgg ggtaattttt actaatttca tg                                     32
```